US010624894B2

United States Patent
Cederlund et al.

(10) Patent No.: US 10,624,894 B2
(45) Date of Patent: Apr. 21, 2020

(54) PHARMACEUTICAL PRODUCT AND COMMUNICATION TOOL

(71) Applicant: ScientificMed Sweden AB, Stockholm (SE)

(72) Inventors: Johan Cederlund, Bromma (SE); Jan Fjellstrom, Stockholm (SE)

(73) Assignee: ScientificMed Sweden AB, Stockholm (SE)

( * ) Notice: Subject to any disclaimer, the term of this patent is extended or adjusted under 35 U.S.C. 154(b) by 0 days.

(21) Appl. No.: 16/158,494

(22) Filed: Oct. 12, 2018

(65) Prior Publication Data
US 2019/0091228 A1    Mar. 28, 2019

Related U.S. Application Data

(63) Continuation of application No. 14/842,374, filed on Sep. 1, 2015, now abandoned, which is a
(Continued)

(30) Foreign Application Priority Data

Jan. 21, 2011   (EP) ..................... 11151683

(51) Int. Cl.
*A61K 31/519*      (2006.01)
*G16H 10/20*       (2018.01)
(Continued)

(52) U.S. Cl.
CPC ............ *A61K 31/519* (2013.01); *G06F 19/00* (2013.01); *G06F 19/324* (2013.01); *G16H 10/20* (2018.01); *G16H 70/00* (2018.01); *G16Z 99/00* (2019.02)

(58) Field of Classification Search
None
See application file for complete search history.

(56) References Cited

U.S. PATENT DOCUMENTS

| 2002/0032581 | A1* | 3/2002 | Reitberg | G06F 19/3456 705/2 |
| 2002/0035486 | A1* | 3/2002 | Huyn | G06F 19/3418 705/3 |

(Continued)

FOREIGN PATENT DOCUMENTS

WO    02095352 A2    11/2002

OTHER PUBLICATIONS

Liu "Evidence-Based Medicine Review: Plato Trial" California Pharmacist; Spring 2010; pp. 46-48.
(Continued)

*Primary Examiner* — Michael Tomaszewski
(74) *Attorney, Agent, or Firm* — Pierce Atwood LLP; Kevin M. Farrell

(57) ABSTRACT

The present invention relates to a substance with pharmaceutical activity against a medical condition for use in a treatment of said medical condition in combination with a computer program product comprising instructions causing a computer to perform a method comprising the steps
 providing a patient with a set of questions according to a question schedule, wherein said set of questions is specific to the pharmaceutical product;
 collecting answers to said questions from said patient;
 subjecting said answers to a set of functions specific for the set of questions and the pharmaceutical product thereby generating patient specific feedback information;
 providing said feedback information to the patient; and
 optionally extracting clinically relevant information from said answers and providing said clinically relevant information to a database adapted for collecting clinically relevant information during clinical use of said substance. The invention further relates to a corresponding kit-of-parts comprising the substance and the
(Continued)

computer program product, and the computer program product and its method as such.

18 Claims, 13 Drawing Sheets

Related U.S. Application Data continuation-in-part of application No. 13/980,611, filed as application No. PCT/EP2012/050908 on Jan. 20, 2012, now abandoned.

(60) Provisional application No. 61/435,079, filed on Jan. 21, 2011.

(51) Int. Cl.
*G06F 19/00* (2018.01)
*G16Z 99/00* (2019.01)
*G16H 70/00* (2018.01)

(56) References Cited

U.S. PATENT DOCUMENTS

| | | | |
|---|---|---|---|
| 2006/0224326 A1* | 10/2006 | St. Ores | G16H 10/20 702/19 |
| 2006/0281977 A1* | 12/2006 | Soppet | G06F 19/3481 600/300 |
| 2009/0234240 A1 | 9/2009 | Kuenzler et al. | |

OTHER PUBLICATIONS

U.S. Department of Health and Human Services Food and Drug Administration; "Guidance for Industry, Patient-Outcome Measures: use in Medical Product Development to Support Labelling Claims" 2009; available at http://www.fda.gov/downloads/Drugs/GuidanceComplianceRegulatorvInformation/Guidances/UCM193282.pdf.

Wild, et al. "Principles of Good Practice for the Translation and Cultural Adaptation Process for Patient-Reported Outcomes (PRO) Measures: Report of the ISPOR Task Force for Translation and Cultural Adaptation" Value in Health; vol. 8; No. 2; 2005; pp. 94-104.

McCann, et al. "Patients' perceptions and experiences of using a mobile phone-based advanced symptom management system (ASyMS) to monitor and manage chemotherapy related toxicity" European Journal of Cancer Care; vol. 18; 2009; pp. 156-164.

European Medicines Agency; Summary of the European Public Assessment Report (EPAR) for Lyrica; Apr. 2010.

Sheehan, et al. "Differences in medication adherence and healthcare resource utilization patterns: older versus newer antidepressant agents in patients with depression and/or anxiety disorders" CNS Drugs; 2008; vol. 22; No. 11; pp. 963-973.

Stein, et al. "Antidepressant Adherence and Medical Resource Use Among Managed Care Patients with Anxiety Disorders" Psychiatric Services; vol. 57; No. 5; May 2006; pp. 673-680.

World Health Organization 2003 Report: "Adherence to long-term therapies: Evidence for Action" available at http://whqlibdoc.who.int/publications/2003/924154992.pdf.

\* cited by examiner

Fig 5
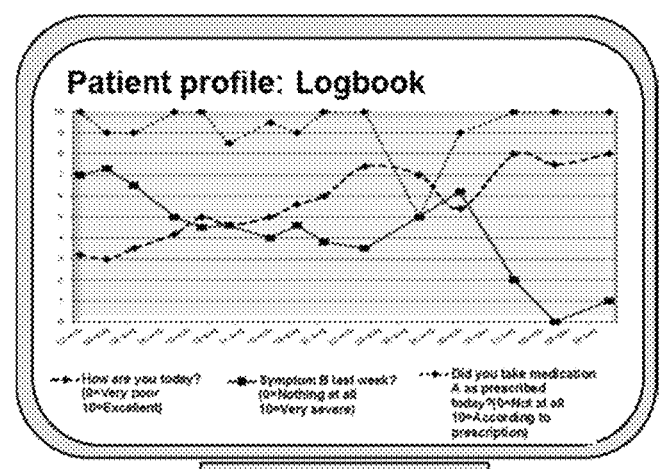
C
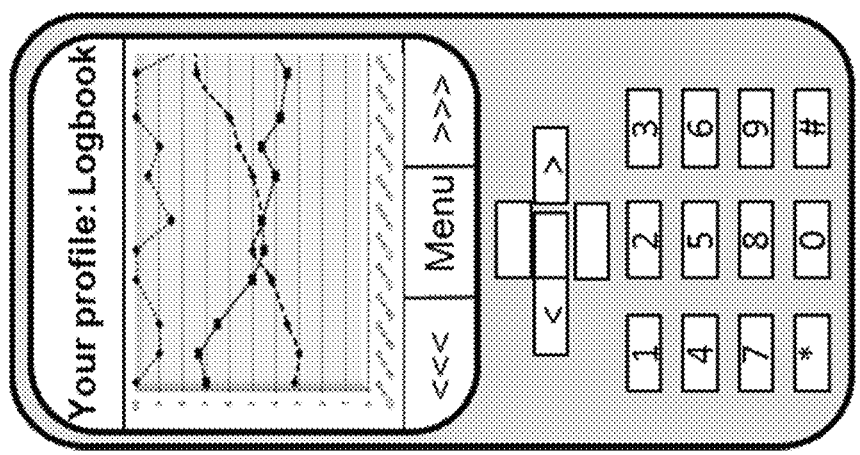
B
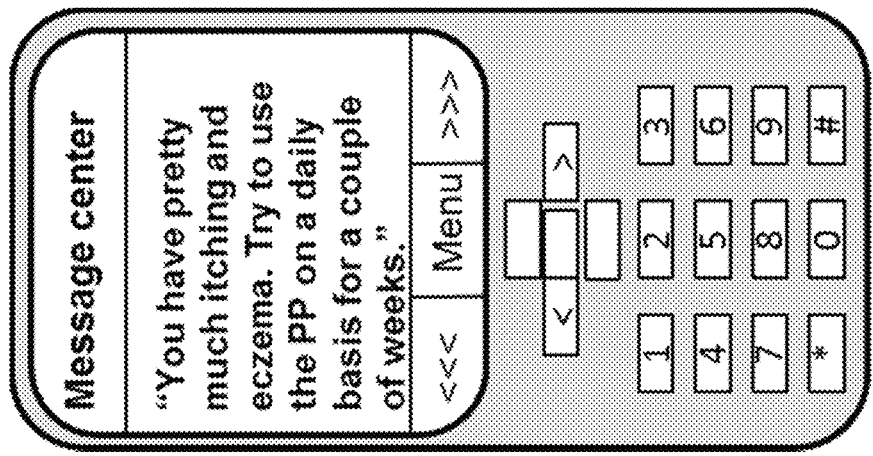
A

-O- How did you sleep last night? 0=Very poorly, 10=Very well
-■- What was you blood glucose level before breakfast? [mmol/l]

-○- How much eczema do you have right now? 0=No eczema, 10=Worst possible
-■- How much itching did you have the last day and night? 0=Nothing at all, 10=Very severe
-◇- How does the treatment practically work out for you? 0=Very bad, 10=Very good

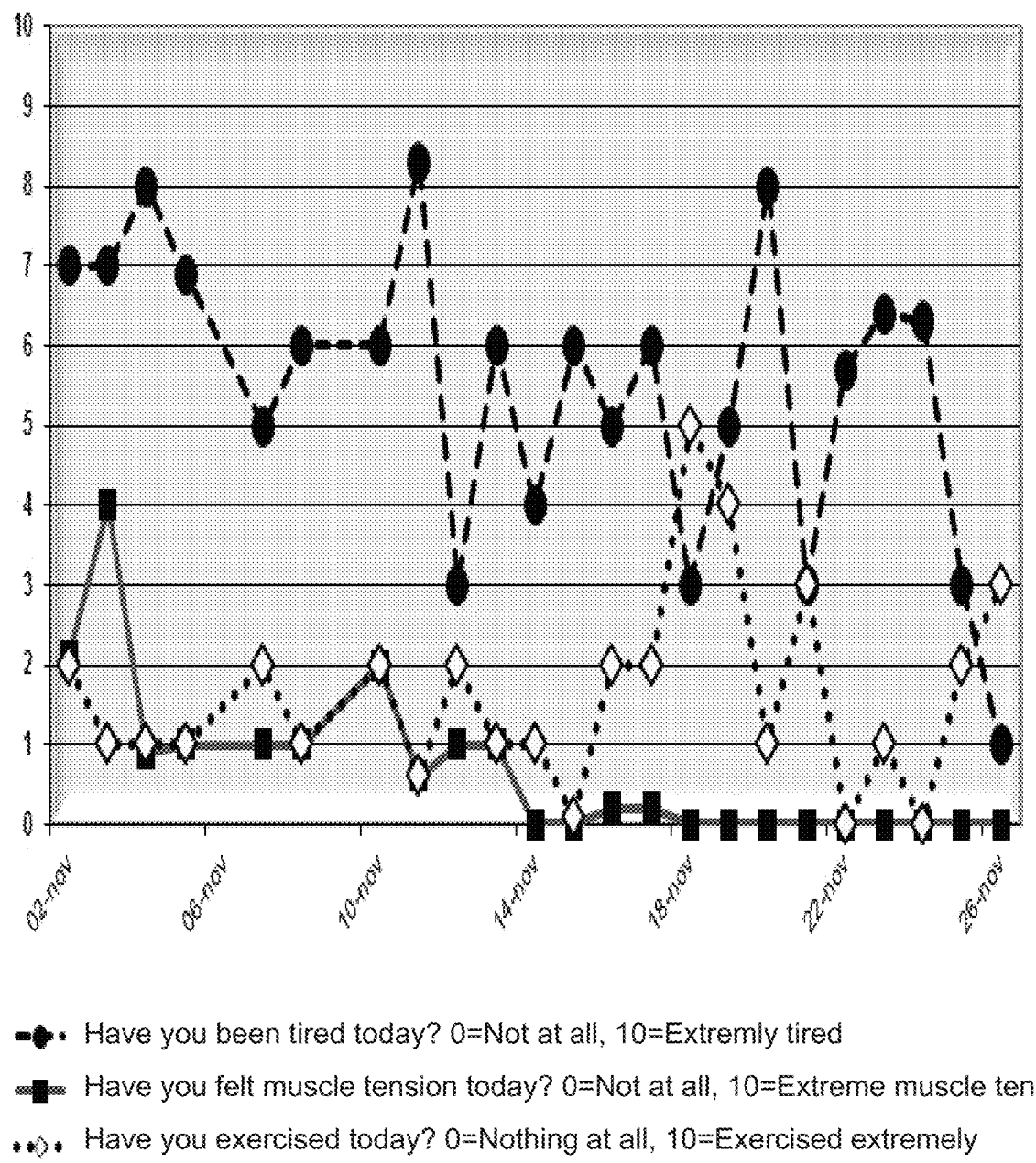

PHARMACEUTICAL PRODUCT AND COMMUNICATION TOOL

FIELD OF THE INVENTION

The present invention relates to the field of drug administration, and particularly to combination products for management and follow-up of drug administration.

BACKGROUND

Drugs on the market today are thoroughly tested with regard to their efficacy and safety during extensive clinical trials before they are approved for marketing by a national or regional Medical Products Agency, such as EMA in Europe or FDA in the U.S.

An important aspect of the clinical trials is to achieve an optimal dosage and administration regimen and these aspects are strictly controlled and monitored during the trials. During clinical trials the manufacturers of a drug collect a large amount of data on the drug. However, once the drug is on the market the control of the dosage is in many cases left to the patient undergoing therapy. This may lead to difficulties in individualizing the used dosage of pharmaceutical products to patient specific conditions and lack of compliance to the prescribed dosing, such as under-dosage, over-dosage and gaps in the administration regimen, which leads to unsatisfactory therapeutic results of the treatment.

Drugs on the market today are stand alone products without any support or connection to the vast amount of data generated during the research and development phase of the product, which could be used for simplifying and optimizing the relation between patient needs and pharmaceutical product clinical conditions. The guidance for matching patient specific conditions to the use of pharmaceutical products is limited.

One of the major issues to reach an increased clinical effect of pharmaceutical treatments in clinical practice is to improve adherence to prescribed medication, see World Health Organisation 2003 Report: Adherence to long-term therapies; Evidence for action: whqlibdoc.who.int/publications/2003/9241545992.pdf Due to the lack of adherence to medication the results of pharmaceutical treatments in clinical practice have difficulties in reaching the same results in clinical effect as the ones made in clinical trials during the development of the pharmaceutical products.

In regulations from FDA and EMA focus on patient safety and follow-up of side effects, as well as possible adverse events, regarding pharmaceuticals is crucial. In clinical practice, however, this is difficult to achieve and a major responsibility is on the patient with little or no support to accomplish it properly.

Even though the safety concerns of medications are directly related to the specific pharmaceutical products, today there are very limited features, or no features, at all integrated with the pharmaceutical product aiming at improving the patient safety concerns of the product. The major responsibility for patient safety for specific pharmaceutical products is on the patients themselves.

Medical devices enhancing the therapeutic effect of drugs are known. For instance, specifically designed inhalers are used to administer various anti-asthmatic drugs and implantable devices have been used for controlled release of anti-cancer drugs.

Patient compliance and monitoring systems are known in the art, e.g. WO02095352. Such systems are focused on monitoring patient compliance and reporting to the medical practitioner and the patient how the treatment is progressing. The system disclosed in WO02095352 is relevant for a certain condition (menopause) and a general therapy (hormone replacement therapy). It is not specifically adapted for a certain pharmaceutical product.

Patient-reported outcome (PRO) measures are used in medical product development and sometimes used to support labelling claims, see U.S. Department of Health and Human Services Food and Drug Administration. *Guidance for Industry. Patient-Reported Outcome Measures: use in Medical Product Development to Support Labelling Claims,* 2009, www.fda.gov/downloads/Drugs/GuidanceComplianceRegulatoryInformation/Guidances/UCM193282.pdf.

A further development of PRO:s is the concept of electronic PRO:s, ePRO:s, which nowadays are partly accepted within clinical practice. One example of such an ePRO is described in McCann et al, European Journal of Cancer Care, 18, 156-164. The system described by McCann et al is however adapted to a chemotherapy in general and not integrated with a specific pharmaceutical product.

SUMMARY OF THE INVENTION

As stated above, large amounts of data on a pharmaceutical product are collected during clinical trials performed by the manufacturers of the pharmaceutical product. The amount of data is generally too large to be kept in the mind of a single person and is summarised by various methods into guidelines for use, such as dosage regimens, counter-indications and risks for side effects and adverse events.

A medical practitioner prescribing the pharmaceutical product, as well as a pharmacist selling a prescription or non-prescription pharmaceutical product, will have a certain knowledge of the product. In some countries lacking adequate regulations, pharmaceuticals may even be provided to patients by persons without proper pharmaceutical or medical training. The providing person's knowledge of the pharmaceutical product is based mainly on the manufacturer's information, which in turn is based on the summaries of the amount of data collected during clinical trials. The providing person may further be highly specialised in the use of the product, such as a researcher with a special interest in the product and the disease it is aimed at treating, but is more likely to be a practitioner that on a daily basis treats patients with very disparate conditions and diseases. Such a practitioner may need to stay current with information on hundreds of various pharmaceutical products. This entails that certain information, such as recently discovered information, on the product may be overlooked or unknown to the providing person.

The present invention is based on the realization that the integral combination of a pharmaceutical product and a specifically adapted system for receiving information from a user of the pharmaceutical product and providing feedback to said user can be used to achieve a number of benefits in clinical practice. In this way, a patient using the pharmaceutical product can directly benefit from the entire body of knowledge, such as clinical data, related to the pharmaceutical product in the possession of the manufacturer or supplier of the pharmaceutical product, in addition to the information provided by the medical practitioner and/or pharmacist providing the pharmaceutical product.

One aspect of the invention is a substance with pharmaceutical activity against a medical condition for use in a treatment of said medical condition in combination with a computer program product comprising instructions causing a computer to perform a method comprising the steps providing a patient with a set of questions according to a question schedule, wherein said set of questions is specific to the pharmaceutical product;

collecting answers to said questions from said patient;

subjecting said answers to a set of functions specific for the set of questions and the pharmaceutical product thereby generating patient-specific feedback information;

providing said feedback information to the patient; and optionally extracting clinically relevant information from said answers and providing said clinically relevant information to a database adapted for collecting clinically relevant information during clinical use of said substance.

In this way, the clinical value of the pharmaceutical product is enhanced to encompass a complete treatment of a medical condition and not just being a product without support or knowledge based features.

One aspect of the invention is a combination product, or a kit-of-parts, comprising the drug in question and a computer program product comprising instructions causing a computer to provide the patient with the questions, receiving answers to the questions, processing the answers and providing feedback to the patient.

One aspect of the invention is a method of treatment of a medical condition with a substance having a pharmaceutical activity against said medical condition in combination with a computer program product comprising instructions causing a computer to provide the patient with the questions, receiving answers to the questions, processing the answers and providing feedback to the patient.

The above three aspects of the invention shall be considered as equivalent unless specifically indicated otherwise. In particular, the characteristics of the pharmaceutical products and computer program products are the same in all three aspects.

Another aspect of the invention is to make clinically relevant information obtained during clinical use, i.e. clinical trials or clinical practice, of the pharmaceutical product come to the benefit of individual patients in a more efficient way. This is realized by continuously updating the Question-Feedback Model implemented in the Computer Program Product by including therein instructions causing the computer to perform a method comprising the steps a) providing a patient and optionally a further respondent with sets of questions according to a question schedule, wherein said sets of questions are specific to the pharmaceutical product;

b) collecting answers to said questions from said patient and optionally said further respondent;

c) subjecting said answers to a set of functions specific for the sets of questions and the pharmaceutical product thereby generating patient-specific feedback information;

d) providing said feedback information to the patient and optionally to the further respondent;

e) extracting clinically relevant information from said answers and providing said clinically relevant information to a database adapted for collecting clinically relevant information during clinical use of said substance;

f) obtaining a revised set of questions and/or a revised set of functions by subjecting the sets of questions and/or the sets of functions to a review based on clinically relevant information collected during clinical use of the substance; and g) repeating steps a)-f) for the duration of said treatment.

The information on which the review is based could be collected from the individual patient or from more than one patient, preferably at least 50%, such as at least 75% or substantially 100% of patients, clinically using said substance in combination with said computer program product. Revision of the set of functions may include a revision of the feedback information and type of feedback given to the patient.

One aspect of the invention is to enhance the match between the specific conditions for each particular patient, both concerning behavioural and physiological aspects, with the clinical conditions for the specific pharmaceutical product concerning used dosage, identified side effects and adverse events, and clinical effect in order to improve individualization. This may be done by including existing clinical research data for the pharmaceutical product in the combination product.

One aspect of the invention is to enhance patient compliance to the prescribed dosage or administration regimen and to enhance the clinical efficacy of the pharmaceutical product. This may be done by including questions on the actual administration; actual dosage; perceived and/or measured therapeutic effects; test results and/or perceived quality of life and providing the patient with feedback correlating the positive effects of the pharmaceutical product, and/or the absence or low prevalence of negative effects, with compliance to the prescribed dosage or administration regimen.

One aspect of the invention is to give the user early indications of the occurrence or development of a possible adverse event and/or side effect, by including questions relating to occurrence or development of a possible adverse event and/or side effect. This increased awareness of adverse events and side effects results in enhanced protection of patients from adverse events and side effects. This may enable an increased patient safety, which is demanded from authorities like EMA and FDA on pharmaceutical products. This may enable early introduction of pharmaceutical products with an incomplete safety profile on the market, since it allows for making each user of the pharmaceutical product aware of the occurrence or development of a possible adverse event and/or side effect and also facilitates that this may be reported directly to medical staff. It may also enable re-introduction of products withdrawn from the market due to an unacceptably high frequency of adverse events or side effects by making each user of the pharmaceutical product aware of the occurrence or development of a possible adverse event and/or side effect at an early stage.

One aspect of the invention is to enhance the patient's quality of life.

One aspect of the invention is to reduce patient mortality during ticagrelor treatment.

One aspect of the invention is to improve patient adherence to a prescribed ticagrelor dosage regimen during ticagrelor treatment.

One aspect of the invention is to reduce Body Mass Index of a patient during ticagrelor treatment.

One aspect of the invention is to aid a patient in smoking cessation during ticagrelor treatment.

One aspect of the invention is to enhance patient assessed quality of life during ticagrelor treatment.

One aspect of the invention is to lower blood levels of Low Density Lipoprotein (LDL) in a patient during ticagrelor treatment.

One aspect of the invention is to increase physical activity in a patient population during ticagrelor treatment.

The computer program product is preferably adapted to be installed on a handheld device, such as a mobile telephone, a Personal Digital Assistant (PDA), tablet computer or similar devices. The computer program product may also be installed on a remote computer, e.g. a server, web or cloud-based service, and accessible to the user through a computer such as a handheld device, a stationary computer, a laptop or the like. In such a case the feedback is also preferably provided through the same device.

Other aspects of the invention are the computer program product itself and the method performed by the computer program product.

Other aspects of the invention are as provided in the appended claims.

BRIEF DESCRIPTION OF THE DRAWINGS

FIG. 5 shows examples of patient specific feedback. (A) Text message to patient (B) Graphs with patient specific data (C) Graphs with patient specific data, user interface on a regular computer.

FIG. 13 shows an illustrative example of one of the patient's feedback graphs from study 3 in the examples

DEFINITIONS

Figure 1:
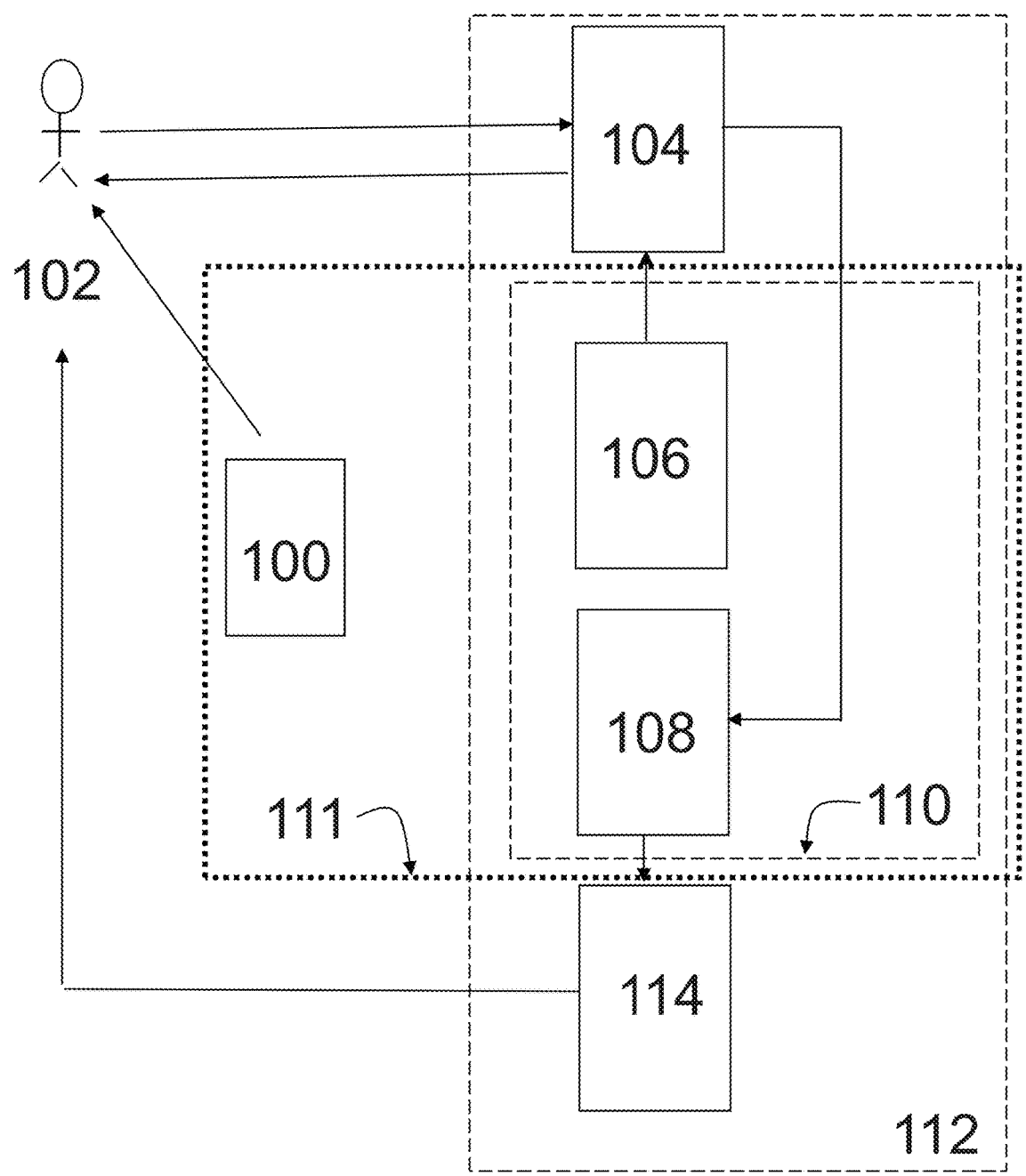
FIG. 1 is a schematic overview of the combination product according to the invention.

All words and terms used in the present specification are intended to have the meaning usually given to them in the relevant art. However, for the sake of clarity, a few terms are specifically defined below.

The term "set of questions" is a questionnaire with predetermined questions or items shown to a respondent to get answers for feedback purposes. The questions within the set preferably have a limited number of possible answers, such as yes/no; scale 1-10; multiple choice; etc. The questions may however also have an undefined number of answers, such as a value of a test parameter (e.g. blood pressure, blood glucose level).

The questions in the set of question are posed to the respondent according to a certain regimen or schedule. This is denoted a "question schedule" or "question regimen" in the present application. These terms are intended to be equivalent if not otherwise indicated.

The term "set of functions" means a set of functions that can be applied to the answers to a set of questions to extract specified information and generate feedback based on the answers.

The combination of a set of questions and a set of functions is referred to as a "question-feedback model", sometimes abbreviated "QFM".

That a set of questions is "specific" to a certain pharmaceutical product shall be construed to mean that it comprises questions that are applicable and clinically relevant to the pharmaceutical product. The individual questions, and the set of questions in total, are preferably more applicable and clinically relevant to the pharmaceutical product in question than to any other pharmaceutical product.

The term "respondent" is used to denote the individual responding to a question.

The term "patient" is used to denote the individual using the pharmaceutical product.

The terms "pharmaceutical product" and "medical product" shall be considered equivalent unless specifically indicated otherwise. These terms refer to pharmaceutically acceptable compositions of pharmaceutically active substances (drugs) intended for administration to a patient.

The term "side effect" means a secondary and usually adverse effect of a drug or treatment.

The term "adverse event" means an adverse outcome that occurs during or after the use of a drug or other intervention but is not necessarily caused by it.

"Clinical use" shall be construed as the use of the pharmaceutical product by individual subjects. It includes the use of the pharmaceutical product in Phase I, II and III clinical trials and the use of the product in patients in clinical practice (sometimes referred to as Phase IV clinical trial).

"Clinically relevant information" shall be construed as information relevant to the clinical characteristics of a pharmaceutical product, e.g. on effect, side effects, counter-indications, metabolism etc. Such information is extensively collected during clinical trials.

DETAILED DESCRIPTION OF THE INVENTION

The main aspect of the present invention is a combination product comprising a pharmaceutical product and a computer program product comprising instructions to perform a method comprising the steps of providing a defined set of specific questions to the user, collecting answers to the questions and analyzing, transforming and processing the answers by way of a defined set of specific functions to generate feedback to the patient.

By adapting the combination of the set of questions and the set of functions, which combination is hereinafter called the "question-feedback model", to be specific to the pharmaceutical product, and optionally the therapeutic indication and/or prescribed dosage/administration regimen, it is possible to achieve an unexpected and significant improvement in the therapeutic effect of the pharmaceutical product and quality of life for patients. Without being bound by theory, the improved therapeutic effect of the pharmaceutical product and quality of life may be due to improved individualization concerning patient specific conditions and clinical aspects of the pharmaceutical product, due to improved compliance by the patient to the prescribed administration and/or dosage regimen, due to improved awareness of other factors influencing the relevant condition being treated with the pharmaceutical product, or due to a placebo or placebo-like effect.

For each combination of the computer program product and the pharmaceutical product a question-feedback model is developed and adapted to the specific characteristics of the pharmaceutical product and the behavior of the patients within the actual therapeutic area(s). The development of the question-feedback model follows the same general rules for different types of pharmaceutical products, but the specific question-feedback models will be different due to the characteristic of the pharmaceutical product and its clinically relevant information.

The question-feedback model comprises the following parts:

A set of questions specific for the pharmaceutical product. The set of questions is implemented in a questionnaire giving the respondent the ability to choose any of a number of possible answers to each question or enter a number representing a test value. The questions may relate to the following, the list being illustrative and non-exhaustive:

- Side effects and adverse events, such as adverse drug effects
- Compliance to dosage and/or administration regimen, such as if or when the pharmaceutical product has been administered; or what dose was administered.
- Symptoms, such as stiffness; swelling of limbs or joints; fatigue; dizziness; headache; pain; blood in excrement; incontinence; fever; urticaria; rashes; skin irritation; itching; anxiety; dryness of mouth or other mucosa; shortness of breath; coughing; sneezing; rhinitis; irritation; restlessness
- Food and drink consumption, such as meal size; meal frequency; type of diet; satisfaction with diet
- Exercise, such as type, duration, frequency or avoidance of physical exercise
- Mood, such as if the respondent is happy, sad, depressed, anxious, restless, etc.
- Sleep, such as if the patient has slept well; duration or quality of sleep
- Use of tobacco, alcohol and other drugs, such as type and amount of use; urge to use; intention or inclination to quit use; progress or lack of progress in cessation
- Stress, such as perceived stress level; amount of personal quality time or spare time; amount of family quality time
- Body functions, such as function of the gastrointestinal system; mental capacity, muscle strength/weakness; olfactory capacity; cardiovascular capacity
- Treatment, such as if the treatment is perceived as working well; motivation to start or continue treatment
- Quantitative test results, such as blood pressure; body fluid or excrement analysis results; body weight; Body Mass Index; pulse
- General, such as quality of life; feeling of support from family, friends, caregiver The questions within the set preferably have a limited number of possible answers, such as yes/no; Visual Analogue Scale (VAS); Likert scale; multiple choice, including symbols (such as "happy face" and "sad face" to capture mood); etc. The questions may however also have an undefined number of answers, such as a value of a test parameter (e.g. blood pressure, blood glucose level, body temperature, weight) or free text.

Generally, the questions are posed to the patient using the pharmaceutical product because only the patient has the true first-hand knowledge of his or her situation. However, in addition to questions posed to the patient, further questions may be posed to other respondents. These may include family members, relatives or other persons close to the patient. This may be particularly useful for pharmaceutical products used in treatment of psychiatric disorders where the patient's assessment of his or her situation may be incomplete and observations made by another person may be valuable. Questions to be answered by other respondents may belong to the same set of questions as those answered by the patient, but may be implemented in a separate questionnaire.

The specific questions and invitations given to the respondents and the type of questions are adapted to the specific characteristics of the pharmaceutical product and the behavior of the patients within the therapeutic area in order to optimize the clinical effects.

When defining the actual questionnaire it is preferable to develop questions to the respondent in order to identify possible upcoming adverse events, or indications of adverse events, as well as possible upcoming side effects with the purpose of increasing patient safety of the specific pharmaceutical product.

In addition to the set of questions, also a regimen for asking the respondent questions should be developed, including which questions are compulsory to answer, optionally before or after a certain time or within a certain time interval; which questions may be left unanswered; at what time of day the questions will show up for the respondents to answer them; with what frequency the questions shall show up etc. The regimen can be static over time but also change, e.g. the frequency of questions can decrease with time or change depending on the respondent's answers.

In addition to the above described questions it may be advantageous to include messages, which cannot be answered, to the respondent. Such messages may include recommendations, suggestions or information intended to motivate the respondent, e.g. to continue the prescribed dosage regimen although symptoms have disappeared or are less pronounced.

It may furthermore be advantageous to adapt the set of questions and messages and the regimen for asking the questions and providing the messages with regard to cultural differences and the language of the user. Principles for the translation and cultural adaptation process for PRO measures have been described (Wild D, et al., Value Health 2005; 2:94-104) and may be adapted to the present invention by the skilled person.

The question-feedback model further comprises retrieving answers from the respondents in a predefined format suitable for input into the set of functions for generating feedback.

The question-feedback model further comprises a set of functions to generate patient-specific feedback based on the answers of the respondent or respondents. These functions may comprise:

- Calculations resulting in a realistic target for a specific patient to achieve. The target could be based on information given from the results from earlier clinical trials concerning the pharmaceutical product. The target could then, for example, be illustrated as a continuous graph of the predicted development for the patient, given that the prescribed administration or dosage regimen is followed. The illustration of this continuous graph would vary between different pharmaceutical products and therapeutic areas. In some areas it would illustrate the improvement of the condition whereas in other areas, for example, COPD (Chronic Obstructive Pulmonary Disease) where patients slowly degenerates, it would illustrate the lack or relative slowness of degeneration.

Calculations of future predictions for a specific pharmaceutical product and patient, based upon earlier answers from the patient and results from clinical trials and answers from other patients in real life using the actual pharmaceutical product, for example external web and data sources. These future predictions could, for example, be several predictions for each patient, based upon different circumstances in the shape of how the patient changes his/her behavior. An example of this could be if the patient increase the adherence/compliance to the specific pharmaceutical product, the patient will develop in a more positive way concerning specific symptoms of the disease.

Knowledge and rules using, for example, methods for Computer Adaptive Testing and Item Response Theory including adapted databank with the purpose of optimal individualized and personalized medicine. This could, for example, result in an individualized questionnaire for each patient based upon their own characteristics and behavior.

Calculation of trend lines based upon the specific pharmaceutical product and the answers given by the patient.

Rules and thresholds for defining when to give notifications concerning the pharmaceutical product and different kind of issues, e.g. possible adverse events, possible side effects, change dosage regimen, possible interaction of other prescribed drugs etc. These have to be carefully developed and take notice of possible combination between different questions, the evolvement of the answers from patients over time, other possibly used medication, etc.

Patient-specific feed-back is generated by the above described set of functions based on answers supplied by the patient. The feedback may be provided through any medium favorable to the patient, e.g. through a website, a handheld device (mobile phone, tablet computer, PDA, etc), paper, voice, e-mail, telefax, SMS, or corresponding type of message etc.

Examples of feedback are:

Graphs illustrating the answers given by the patient on different selected questions. The graphs may, among other things, illustrate how the patient has evolved over time.

Illustrating the answers from the patient in combination with calculated values such as targets for the patient to reach. The purpose of this type of feedback is, for instance, to motivate the patient to continuous improvements.

Illustrations of how the patient's health status is evolving in comparison to the evolvement of earlier patients using the same pharmaceutical product, for example patients in clinical trials.

Illustrations of how the patient's health status could evolve and the result of it as future prediction, based upon how the patient continues to handle his/her health situation and data from clinical use of the pharmaceutical product. For example, graphs could be used to show how the patient might evolve if the patient increased the adherence/compliance to the medication of the pharmaceutical product.

The, preferably de-identified, answers from the patient in relation to calculations based upon information given from other patients in real life/clinical practice using the pharmaceutical product, specifically selected for the actual circumstance. The purpose of this is, among other things, to encourage the patient to increase the personal health status.

Message sent based upon notifications from the algorithms. This could, for example, be messages concerning possible adverse events, or indications of possible side effects, or possible conclusions that a new dosage for the actual pharmaceutical product might be needed, or positive feedback to the patient to encourage a behavior leading to e.g. better compliance or increased quality of life. Exemplary messages could include messages that the used dosage of the pharmaceutical product should be changed, or that the alcohol consumption is below or above a recommended threshold for the pharmaceutical product, or that the amount of consumed food is high or low in comparison to physical activity, or that the first signs of a side effect appear to be showing and that the patient should be aware of these signs. The invention will hence enable a faster change of used medicines by patients experiencing an adverse event. The patient can receive messages from the healthcare personnel as well through the computer program product, as a result of the feedback given to them.

The questionnaire given to the patient could change based upon the algorithms for CAT and IRT (see above), or other appropriate algorithms or computer implemented methods, in order to individualize the questions for the characteristics of each patient and the pharmaceutical product.

Optionally, feedback may also be provided to other than the patient, such as health care staff (e.g. treating medical practitioner or nurse, pharmacist etc.). Such feedback may include:

Results from notifications from the algorithms, e. g. when an adverse event or a side effect has occurred. This information could, for example, be sent to the responsible healthcare provider and/or authorities such as the Medical Product Agency. The healthcare personnel will then be able to take appropriate adjustments. The graphs and illustrations presented above could be given to the responsible healthcare personnel as well.

Results from continuous results in real clinical trials based upon the answers given by the patients. The invention could hence improve clinical research through continuous follow up of a huge amount of patients for the specific selected pharmaceutical products. The information/answers from the patients would be de-identified and returned to the researching organization. The purpose is to utilize the enormous information in real clinical practice in order to develop improved pharmaceutical products and treatments for patients.

The continuous follow-up of the results from patients will also result in possibilities for an easy evaluation between different kind of treatments, both from a medical and an economic perspective.

The question-feedback model may be adapted to the specific pharmaceutical product by using the information on the pharmaceutical product available from clinical trials carried out in preparation for an application for marketing approval for the pharmaceutical product. Such trials are designed to find all relevant information about the pharmaceutical product and that information can be used to design the set of questions with applicable answers, the set of functions for generating the feedback from the answers, and the form of feedback provided to the patient. The continuous development of the QFM, for a specific pharmaceutical product, should also take into consideration relevant knowledge from clinical practice concerning the specific pharmaceutical product, other studies, patient behavior concerning the specific pharmaceutical product, etc.

Information on the normal effect of the pharmaceutical product can be used to provide the patient with feedback on how he or she achieves a better or worse effect than normal when using the pharmaceutical product. It may also be used to give the patient feedback on how the treated condition would have developed if the pharmaceutical product had not been used, or used to a different extent than the patient is actually using it.

Information on known possible side effects may be used to include questions giving early feedback on occurrence of side effects, which may guide the user to change or cease the administration or dosage regimen according to guidelines based on the information about side effects, or to contact the treating physician if advised.

Information on known counter-indications for using the pharmaceutical product may be used to include questions giving early feedback warning for possible side effects or adverse events. It may be that during treatment with the pharmaceutical product the patient contracts a condition which may lead to an adverse event or side effect in combination with the pharmaceutical product. If such risks are known, it is possible to include questions resulting in feedback making the patient and optionally the treating physician aware of this complication, which may lead to an adjustment or change in treatment implying an improved patient safety of the pharmaceutical product.

For example, one specific pharmaceutical product indicated for treatment of obesity is known to worsen depressions. The majority of questions and feedback in a question-feedback model for an obesity drug would probably focus on diet, physical activity, weight loss and the like. The inclusion of one or more mood-related questions would however be able to indicate early if the patient is at risk of developing a depression which would be a strong indication to the patient to cease the administration of the pharmaceutical product. These questions should be specifically designed to retrieve relevant information on the types of mood-related adverse events or side effects associated with the specific pharmaceutical product.

Optionally, additional information not supplied directly by the patient is used. This may include
  Information from performed clinical trials. This could, for example, be the result how the included patients in the clinical trials using the actual pharmaceutical product responded to the pharmaceutical.
  Information from other patients in clinical practice. This could, for example, be the result and answers given by other patients in real life using the equivalent pharmaceutical product and how they respond to the pharmaceutical. Using that information, a common index of how a huge amount of patients react upon the actual pharmaceutical product in real life can be evaluated, for instance.
  Information from other products and systems, such as administration systems, laboratory data, personal patient devices such as watches, heart rate monitors, scales, mobile phone applications, pedometers, glucose meters, thermometers, audiometers, inhalers, ultrasound devices, electrocardiography devices, etc. Such information can be automatically collected by or transferred to the computer program product by different means.

For each combination of a specific pharmaceutical product and the computer program product a candidate specific question-feedback model has to be developed. This candidate model has to be developed based on all considerations mentioned above.

The development of the candidate question-feedback model includes the following steps:

An optimal set of questions is identified and developed. The intention should be to develop an optimal set of questions and normally this is an iterative process. In this, the following aspects should be considered, as well as the concerns mentioned above describing what is included in the set of questions.
  The set of questions should be designed based upon the specific circumstances of the pharmaceutical product concerning the existence of possible adverse events, possible side effects and the therapeutic effect.
  The set of questions should be designed based upon the special circumstances of the patient category of the actual therapeutic area.
  The set of questions should be designed in order to improve the behavioral aspects of the patients. They should increase the possibilities for enhanced clinical effect and patient safety of the specific pharmaceutical product, and the quality of life for the patients.
  The questions should be easy to understand and encourage the patient to answer them. The suitable and optimal structure type of questions should be used, i.e. VAS, Likert scale, free text, multiple choice, etc.
  The amount of questions should be minimized in order to simplify for the patients.
  The proper regimen for asking the respondent questions should be developed. The following should, for example, be defined:
    When the questions should appear in the patient's device, for instance which specific day and what time during the day
    Which questions that should be compulsory to answer
    The frequency of how often the questions should appear in the patient's device
  Which questions that should be able to individualize, i.e. to add or remove, and to which extent. For example, some questions could be able to appear more or less seldom, i.e. changing the frequency of the question. Possibilities to support life style changes of the patients, central to the specific pharmaceutical product, e.g. within the metabolic syndrome for cardiovascular pharmaceutical products.
  Whether, and in which way, the set of questions should be individualized and adopted based upon patient and pharmaceutical product specific conditions. This could involve how the questions should be answered, selection of media, etc, with the purpose of improving the clinical effect and patient safety of the specific pharmaceutical product.

An optimal set of functions is identified and developed. The intention should be to develop an optimal set of functions and normally this is an iterative process. In this, the following aspects should be considered, as well as the concerns mentioned above describing what is included in the set of functions.
  The set of functions should be designed based upon the specific circumstances of the pharmaceutical product concerning the existence of possible adverse events, possible side effects and the therapeutic effect.

The set of functions should be designed based upon the special circumstances of the patient category of the actual therapeutic area.

The set of functions should be designed in order to improve the behavioral aspects of the patients. They should increase the possibilities for enhanced clinical effect and patient safety of the specific pharmaceutical product, and the quality of life for the patients.

The set of functions should be developed based upon which type of information that is possible to use considering the specific pharmaceutical product, e.g. if there are information from earlier clinical trials and/or if information from other patients in clinical practice, that can be utilized.

The set of functions should be developed based upon whether knowledge and rules from methods using Item Response Theory and Computer Adaptive Testing, or other appropriate algorithms or computer implemented methods, are available.

The set of functions concerning rules and thresholds, for example with the purpose of avoiding possible adverse events and/or side effects, giving positive feedback and optimizing the dosage regimen, should be developed concerning the circumstances of the pharmaceutical product, performed clinical trials and the specific patient population.

The set of functions could contain rules of which questions should be related to specific thresholds, for example if a threshold is reached by a patient, which questions should then appear or which type of feedback should be given The set of functions could contain dependencies between certain questions and the functionality and rules of the dependencies, e.g. if a patient answers a specific alternative on one question another specific question appear, otherwise another question will appear instead.

The set of functions could contain the administration rules concerning different intervals when specific questions will appear based on a certain threshold, which could be time or that a criterion has been fulfilled. An example of this is that during a first period of time the patient could have a certain set of questions, and after a certain time, which could be a couple of weeks or months, the set of questions changes into another version. The set of questions could also be changed due to a certain threshold has been fulfilled, for example a certain level of blood pressure or the level of HbA1c is reached.

An optimal type of feedback should be identified and developed. The intention should be to develop an optimal type of feedback and normally this is an iterative process. In this, the following aspects should be considered, as well as the concerns mentioned above describing what is included in the type of feedback.

The type of feedback should be designed based upon the specific circumstances of the pharmaceutical product concerning the existence of possible adverse events, possible side effects, and the therapeutic effect.

The type of feedback should be designed based upon the special circumstances of the patient category of the actual therapeutic area.

The type of feedback should be designed in order to improve the behavioral aspects of the patients. They should increase the possibilities for enhanced clinical effect and patient safety of the specific pharmaceutical product, and the quality of life for the patients.

It should be defined which type of feedback that should be given to whom.

The type of feedback should be designed and developed based upon whom to which the feedback should be given to.

The type of feedback should be designed and developed based upon the developed set of questions and set of functions for the specific question-feedback model.

The type of feedback could be designed to improve the clinical effect and patient safety of the specific pharmaceutical product in using the given thresholds The type of feedback could be designed in order to improve the clinical effect and patient safety of the specific pharmaceutical product by individualizing the dosage administration of the specific pharmaceutical product to the conditions of the patient It may be desirable to furthermore optimize the set of questions and the feedback for use on a certain computer platform. For instance, if the respondent will use a simple mobile telephone the questions will be adapted so that they can be answered simply by pressing buttons 0-9 and yes/no/up/down and feedback may be provided in short text messages and simple graphs. If the respondent uses an advanced mobile telephone or tablet computer the questions may be constructed to give more complex answers and still be easy to use, and the feedback may also be made more complex, such as color-coded graphs and longer messages.

The candidate question-feedback model is then validated in one or more steps. The validation of the model aims to evaluate and ensure the therapeutic effect of the integrated combination of the computer program product and pharmaceutical product, minimize the amount of adverse events and side effects, and increase the quality of life for the patients. The evaluation of the clinical efficacy and value of the candidate question-feedback model for a specific pharmaceutical product is preferably performed through clinical trials, in what is usually referred to as a Phase II clinical trial or a corresponding study. In this the candidate question-feedback model for the pharmaceutical product is evaluated concerning clinical efficacy such as positive medical efficacy and increased security level for the combination product.

There are a number of types and designs of clinical trials and a skilled person would be able to choose a type of trial and design well suited to achieve the aims as outlined herein. The clinical trials or corresponding study should be designed to focus to prove the following of the model enabling the combination of the computer program product and the pharmaceutical product:

achieve optimum medical efficacy of the combined product achieve optimum level of safety for patients increase quality of life for the patient Based on progress and results from clinical trials and clinical practice, the question-feedback model may of course be adjusted or revised in order to improve its efficacy, safety or other aspects of quality.

The combination of the question-feedback model and the pharmaceutical product may also be compared to an existing approved treatment in a Phase III-type clinical trial before being put on the market.

The question-feedback model is implemented in one or more computer-program products running on one or more computer platforms, wherein the computer program product and the computer platform together have means for providing the set of questions, for receiving the answers, for applying the set of functions to generate the patient-specific feedback and preferably also for providing said feedback to the patient.

The computer program product may be supplied on a suitable carrier together with the pharmaceutical product, as a kit-of-parts. Suitable carriers are well-known to the skilled person and depend on the platform on which the computer program product shall run, but includes without limitation, CD-ROM, USB-memory sticks, flash memory cards. The computer program product may also be made available to the end user separately from the physical pharmaceutical product. This can be done e.g. by supplying information on how to access the computer program product on a remote server and install the computer program product on the relevant platform with the pharmaceutical product. The computer program product could also run on a remote server and be accessed via an internet service using a user interface like a web browser or client application for the relevant platform. Ways of accessing and implementing the computer program product could also include barcode scanning techniques. The computer program product may be included in the kit-of-parts in the form of instructions for accessing and/or installing the computer program product from a remote location, such as a remote server. Information about how to get started with the computer program product and how to use it could be given in the instructions related to the pharmaceutical product or the computer program product.

If the computer program product is made available separately from the pharmaceutical product, a unique identifier may be provided with each individual kit. The identifier may be used to confirm that the respondent has got the correct combination of computer program product and pharmaceutical product and to confirm that the respondent has the right to use the computer program product.

The computer program product is an essential part of the main aspect of the invention and is itself one aspect of the invention, as is the method implemented in the computer program product.

The pharmaceutical product may be any pharmaceutical product for which there exists a preferred or prescribed administration and/or dosage regimen. This includes all pharmaceutical products that have been approved for marketing based on results of clinical trials defining a therapeutically effective dose or dose range and pharmaceutical products for which a medical or other practitioner prescribes an individual administration or dosage regimen to an individual patient based on information supplied by the manufacturer of the pharmaceutical product. It furthermore includes pharmaceutical products for which an application for marketing approval is to be submitted, pending, or has been refused. The pharmaceutical product may or may not be subject to regulation by a Medical Products Agency or other governmental agency, it may be a prescription only product, an over-the-counter product or any other allegedly therapeutically active product, such as a herbal medicinal product.

Examples of pharmaceutical products that can be used in the present invention are (trade names within parentheses) Aripiprazol (Abilify) Rimonabant (Acomplia), Pioglitazon (Actos), glucoseamine (Glucosine), Octocog alfa (Advate, Advair), Flutikason in combination with Salmeterol (Seretide), zolpidem (Ambien, Stilnox), Insulin glulisin (Apidra), Donepezil (Aricept), irbesartan (Avapro, Aprovel), rosiglitazone (Avandia), metformin in combination with rosiglitazone (Avandamet), glimepiride in combination with rosiglitazone (Avandaryl), bevacizumab (Avastin), Interferon beta (Avonex), Darbepoetin alfa (Aranesp), anastrozole (Arimidex), Kandesartan (Atacand), olmesartan (Benicar, Olmetec), Interferon beta-lb (Betaseron), Interferon beta (Betaferon), exenatide (Byetta), Bikalutamid (Casodex), Celecoxib (Celebrex, Celebra), Escitalopram (Cipralex/Lexapro), duloxetine (Cymbalta), Vareniklin (Champix), Glatiramer (Copaxone), Carvedilol (Coreg), Losartan (Cozaar), Rosuvastatin (Crestor), Ramipril (Tritace), Valsartan (Diovan), Venlafaxin (Efexor), oxaliplatin (Eloxatin), Etanercept (Enbrel), raloxifene (Evista), ezetimibe (Ezetrol, Zetia), Tamsulosin (Flomax, Flomaxtra, Urimax), fluticasone (Flovent, Flixotide), Alendronic acid (Fosamax), Gemcitabine (Gemzar), imatinib mesylate (Gleevec, Glivec), Trastuzumab (Herceptin), insulin lispro (Humalog), Adalimumab (Humira), Lopinavir/ritonavir (Kaletra), Sumatriptan (Imitrex, Imigran), Sitagliptin (Januvia), insulin glargin (Lantus), Fenofibrate (Lipanthyl, TriCor), atorvastatin (Lipitor), Insulin Detemir (Levemir), amlodipine and benazepril (Lotrel), Leuprorelin, (Lupron, Leuplin), pregabalin (Lyrica), rituximab (Mabthera, Rituxan), Telmisartan (Micardis), Esomeprazole (Nexium), amlodipine (Norvasc), insulin aspart (NovoLog, NovoMix, NovoRapid), repaglinid (NovoNorm), Rabeprazole (Pariet), paroxetine (Paxil, Seroxat), Pantoprazole (Protonix, Pantozol, Pantoloc), Clopidogrel (Plavix), pravastatin (Pravachol), Epoetin Alfa (Procrit, Eprex), takrolimus (Protopic), budesonid (Pulmicort), interferon beta-la (Rebif), sibutramin (Reductil), Infliximab (Remicade), Risperidon (Risperdal), Metoprolol (Seloken, Toprol), quetiapine (Seroquel), Tiotropium (Spiriva), budesonide and formoterol (Symbicort), Montelukast (Singulair), Docetaxel (Taxotere), Topiramat (Topamax), Emtricitabin and Tenofovirdisoproxil (Truvada), ezetimibe and simvastatin (Vytorin), bupropion (Wellbutrin), Betametason in combination with Kalcipotriol (Xamiol) calcipotriene (Taclonex), simvastatin (Zocor), Sertralin (Zoloft), zoledronic acid (Zometa), Olanzapin (Zyprexa), cetirizine (Zyrtec), ticagrelor (Brilique/Brilinta). The preferred pharmaceutical product is ticagrelor.

In one aspect, the pharmaceutical product is ticagrelor. In this aspect, the set of questions may comprise at least one question relating to the patient's intake of ticagrelor. The answers are subjected to a set of functions generating patient-specific feedback on the adherence to the prescribed ticagrelor dosage regimen, and the thus generated patient-specific feedback is provided to the patient.

The patient specific feedback on adherence comprises a color signal, such as a "traffic light" type signal, i.e. green for good adherence, yellow for adequate adherence and red for poor adherence. The patient specific feedback on adherence may also comprise a graph showing the patient's adherence in the past up to the present time. The graph may show information relating only to a limited time in the past, such as the last month or last week. The patient specific feedback on adherence may also comprise text messages or a numerical value representing the relation between the number of actual ticagrelor doses taken and the prescribed number of ticagrelor doses in a time interval.

When the invention is applied to ticagrelor, the set of questions may further comprise questions relating to at least one of: level of physical activity; weight; smoking habits; blood levels of cholesterol, lipids and/or LDL; blood levels of glucose and/or HbA1c; blood pressure, as set out in Study 5 below.

The invention will now be described in relation to the appended drawings.

FIG. 1 shows a combination product (111) comprising a pharmaceutical product (100) available to a patient/respondent (102) and a computer program product (110). A set of questions (106) and a set of functions (108) for converting the answers to the questions into patient feedback are implemented in the computer program product (110) running on a computer platform (112) having means (104) for receiving answers to said set of questions (106) from said patient (102). The computer platform further has means (114) for receiving patient feedback from the set of functions (108) and communicating said feedback to said patient (102). The combination product according to the invention is designated as 111

Figure 2:
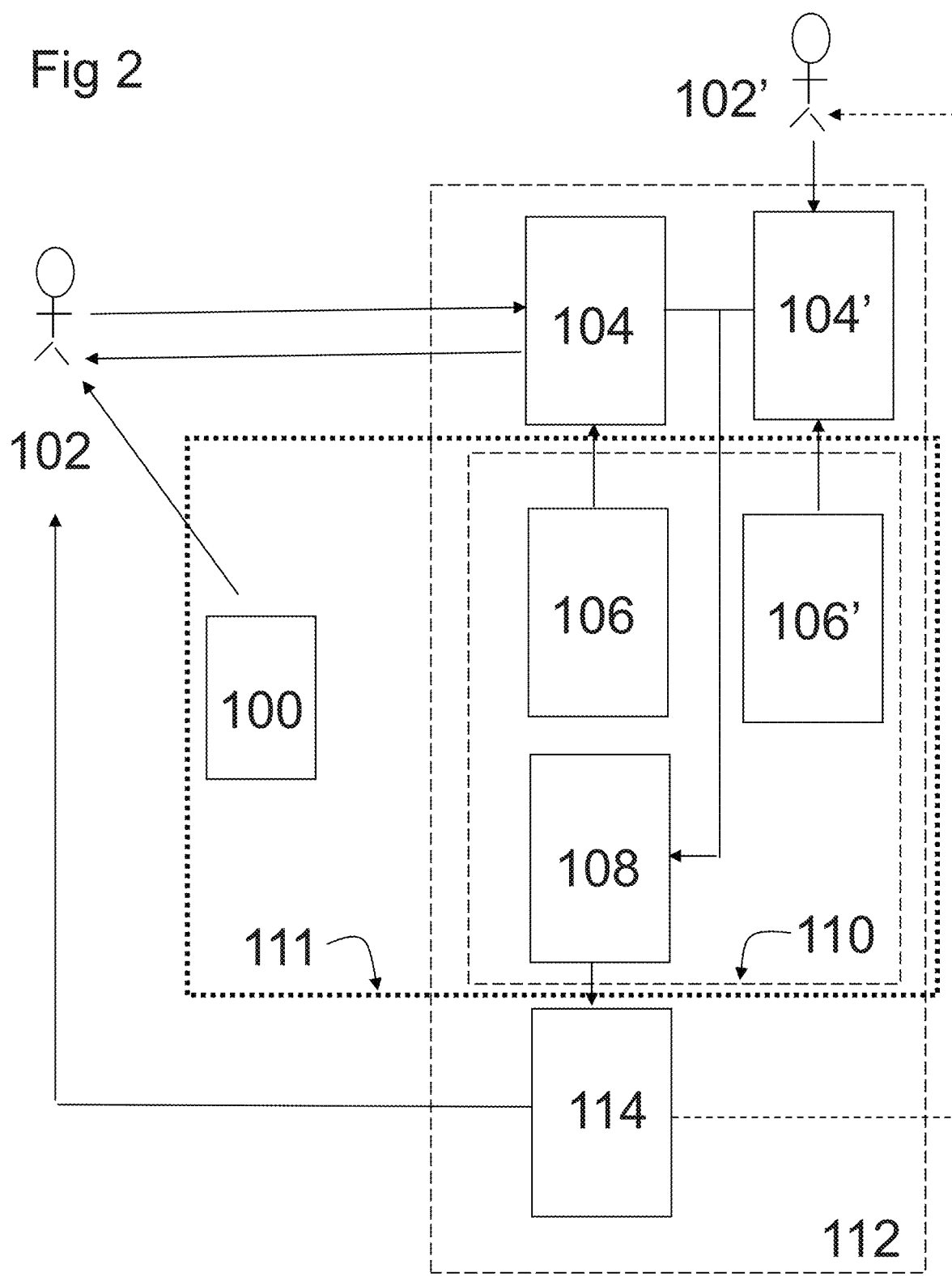
FIG. 2 shows an alternative embodiment of the invention.
Figure 3:
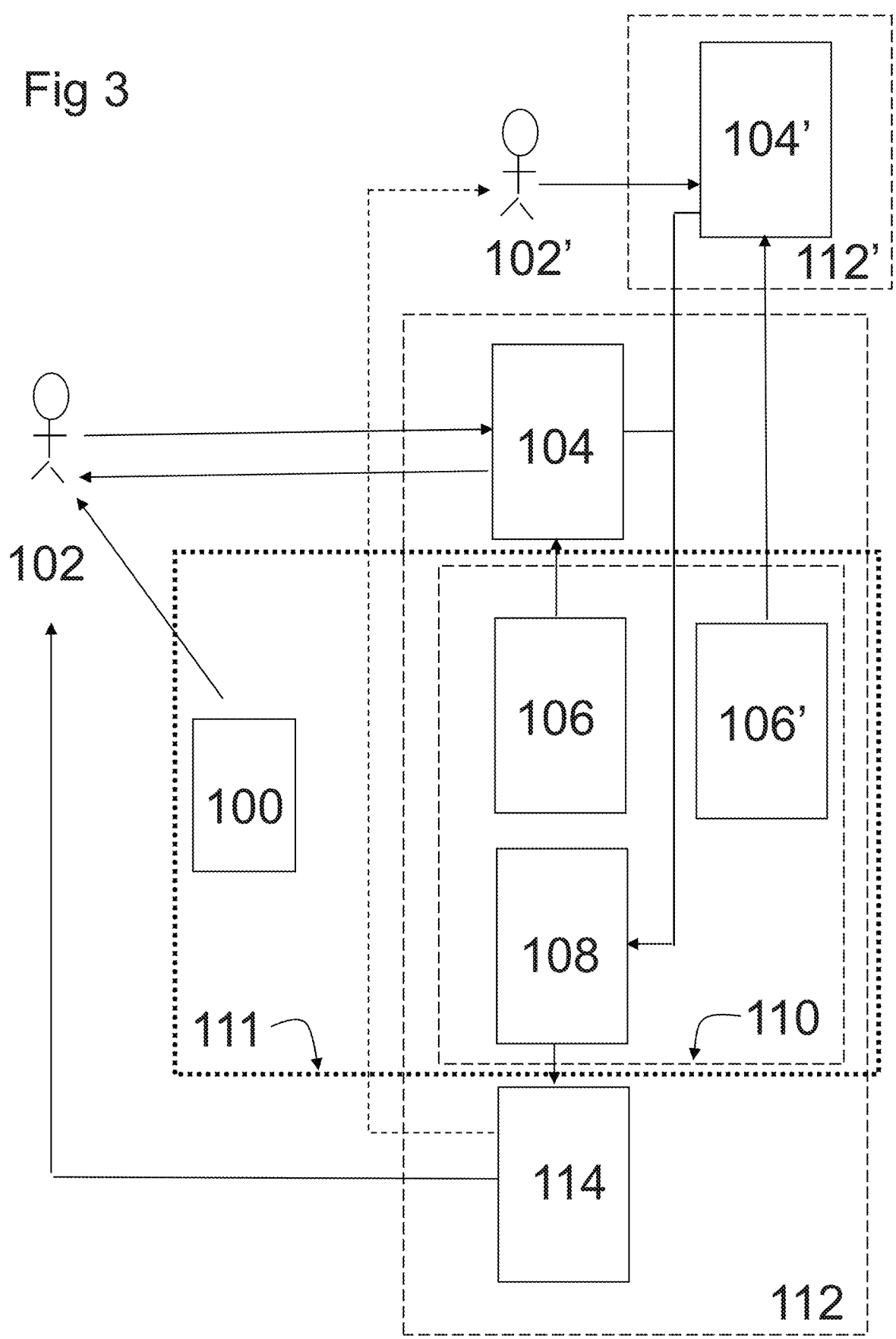
FIG. 3 shows an alternative embodiment of the invention.

FIG. 2 shows an alternative embodiment of the invention, wherein a further respondent (102') answers a second set of questions (106') through means (104') for receiving answers to said set of questions from said further respondent. The answers to the set (106') is then provided together with the answers to the set (106) to the set of functions (108) to generate feedback to patient (102) through computer platform means (114) for receiving patient feedback from the set of functions (108) and communicating said feedback to said patient (102). Optionally, feedback is also provided to the further respondent (102'), shown with a dotted line. The further respondent may be a person close to the patient, such as a family member. The means (104') for receiving answers from the further respondent may be implemented on a separate computer platform (112'), cf FIG. 3.

The examples below serve to further illustrate the invention, provide experimental support and enable the skilled person to work the invention. They shall not be construed as limiting the scope of the invention, which is that defined by the appended claims.

EXAMPLES

The implementation of the invention in clinical practice is described below in four examples relating to various pharmaceutical products aimed at treating various medical conditions. The examples are provided in order to give a further explanation of the invention but are not intended to limit the scope of the invention, which is that of the appended claims.
Common Descriptions for the First Three Studies We initially performed three studies to show how the invention works and the positive effects of the invention as applied to various pharmaceutical products. Studies 1-3 describe the use of an initial QFM that is adapted to the pharmaceutical product but not yet fully optimized. This shows that the invention works and gives a tangible clinical effect. Further optimization of the QFM will yield a better clinical effect.

In the studies the combination product, a computer program product (CPP) integrated with a pharmaceutical product (PP) using an adapted question-feedback model (QFM), were evaluated versus only a PP, respectively versus only a CPP. The overall purpose was to evaluate different aspects of the invention in three different therapeutic areas, and using three different types of a PP, in order to show the effect of the invention.

In order to visualize the study designs, objectives and results as clearly as possible; in the studies the used PP is denoted as the letter "A", the used CPP as the letter "B", and the combination product, i.e., a specific PP in combination with a CPP using an adapted QFM, as the letters "A+B".
General Objectives of the Studies Several important aspects of the invention have been evaluated in the three separate studies in different therapy areas; diabetes, atopic dermatitis, and generalized anxiety disorder (GAD). In table 1 below the different evaluations in the three studies are summarized.

TABLE 1

Summary of the evaluations of the invention

| Evaluation | Therapy area | Effect variable A + B |
|---|---|---|
| Clinical effect of A + B versus only A | Diabetes | Level of HbA1c |
| Clinical effect of A + B versus B | Atopic dermatitis | Primary symptom and side effects |
| Perceived clinical value of A + B over time | Atopic dermatitis | Perceived clinical value of A + B |
| Clinical effect of A + B versus A concerning improved clinical value | GAD | Primary symptoms |
| Clinical effect of A + B versus A concerning improved patient safety | GAD | Primary symptoms and side effects |
| Quality of life of A + B versus only A | GAD | Perceived quality of life |
| Adherence to A when using A + B compared to only A | GAD | Level of adherence to A |

Conclusions and General Aspects Concerning the Results from the Studies

The results from the studies confirm that the invention works and that the combination product, A+B, gives the following positive effects:

1. Improved clinical effect
2. Improved patient safety
3. Increased quality of life For detailed description concerning the specific results, see the study documentation below. One central aspect was the improved efficacy when identifying and realizing an individualized dosage regimen for the given PP. In the GAD study this was clearly illustrated, using the combination product. When the dosage of the used PP was individualized, based on the used QFM, not only was the clinical effect improved but also the patient safety. In this particular case the decisions were to either increase the dosage of the PP or interrupt the usage of it.

Another aspect of the increased clinical effects mentioned above was the increased level of compliance to the prescribed PP, which the use of the combination product led to. This was also illustrated in two different perspectives in the studies of atopic dermatitis and GAD. The former showed an increased perceived level of practical usage and the latter showed an increased adherence.

The improved clinical result, especially when it came to diabetes, was also due to an improved awareness of other factors relevant to the actual therapy area, the patient population and the specific PP. Such factors included levels of physical activity, stress, and food intake. Another aspect of the invention and the results from particularly the GAD study was the central role of the QFM. The QFM had to be specific both to the conditions of the patient category and to the clinical effect of the PP, in order to achieve a better clinical effect than just from the PP alone. In the GAD study it was obvious that the set of functions and feedback were a central part of the invention in order to achieve clinical effect. An example of the opposite situation was the result from one of the Atopic study set-ups, when a patient was using just "B" without an adapted QFM. Another aspect of the invention is the mechanism of improved patient safety regarding side effects, adverse events, and dosage regimen of the specific PP. A key mechanism is to continuously measure, detect, and follow up clinical effect, side effects, and adverse events in clinical practice. Another key mechanism is the increased awareness the measuring (questions and feedback) routine gives the patient about his/her health situation and medical treatment concerning central aspects of the specific PP. Among other things it helps the patient to understand and detect possible side effects and adverse events. The mechanisms form a basis for well-based decision-making for a possible titration, interruption, or other reaction of the medication treatment.

Another aspect of the studies, and in particular the atopic dermatitis study, was the patients' desire for even more feedback regarding the use of the PP.

Another aspect of the three studies was that the invention created improved positive clinical effect concerning PPs in three totally different therapy areas, which shows the great width of the invention. Particularly it is possible to improve clinical effect both in therapy areas where the measurement variables (e.g. symptoms and side effects) are relatively concrete and absolute, such as the situation with diabetes, and in therapy areas where the measurement variables are relatively subjectively, such as the situation with GAD.

Another aspect of the invention and the results is that it is valid for different types of PP. In the three studies the PP had different pharmaceutical compositions; a capsule, an ointment, and an injection.

General Aspects of the Used QFM

Figure 4:
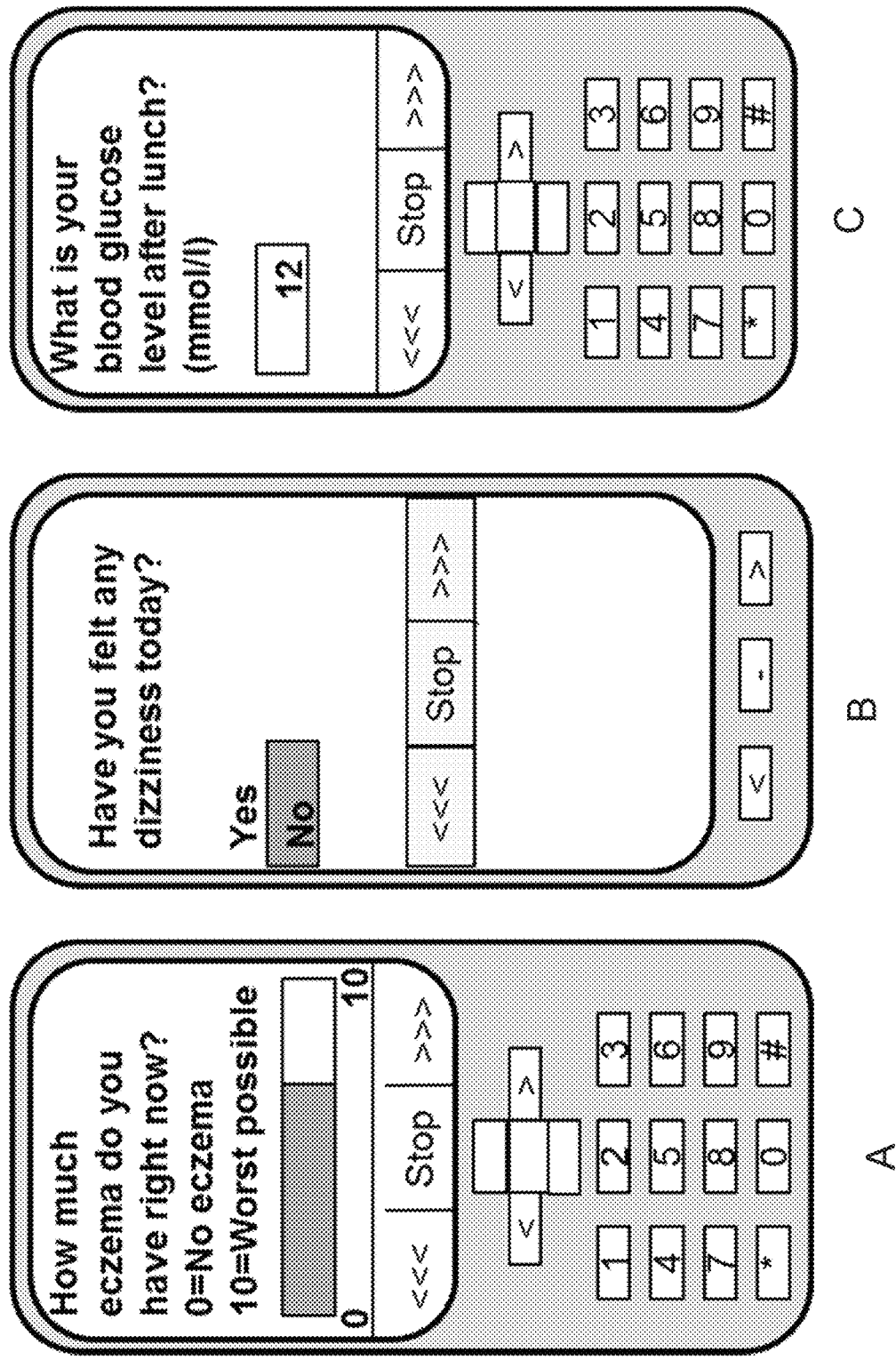
FIG. 4 shows examples of the user interface of the implemented QFM in a regular mobile phone used in the three studies. Questions shown are examples of (A) Visual Analogue scale (B) multiple choice (C) numeric.

In the three studies the respectively used QFM consisted of the following parts:

A set of questions. Some of the characteristics:
  Developed based on the specific aspects of the PP and the patient category.
  One compulsory group of questions to be asked, which was given to all patients, and one optional group of questions to be asked if they were relevant for the individual patient.
  The questions could be individualized depending on the patients' specific conditions and situation. For example, specific questions could be added or removed depending on specific patient conditions.
  Different type of questions, i.e. multiple choice, VAS, etc.
  Both compulsory and optional to answer questions.
  The questions were integrated with a question schedule with response times. The response times included automatic reminders (alerts) in the CPP on the mobile phones to remind the patients to answer the questions. The question schedule was developed so only the questions valid for each response time showed up in the CPP and were possible for the patient to answer. This feature secured that the patients answered the right questions at the right time. The question schedule could be individualized depending on the patient's daily schedule.
  The questions were presented to the patient on the patient's mobile phone. The illustration (FIG. 4) shows examples of the user interface of the implemented QFM in a regular mobile phone used in the three studies. Questions shown are examples of Visual Analogue scale (FIG. 4A), multiple choice (FIG. 4B) and numeric (FIG. 4C).

A set of functions. Some of the characteristics:
  Calculations on the data, consisted of the answers from the patients, in order to present patient specific information in different graphs. Data from different questions were grouped together to visualize important relationships and correlations between variables. Graphs were constructed to show development over time for chosen variables.
  Calculations on the collected and non-collected data, which could trigger SMS reminders to the patients about continuously answering the questions.
  Algorithms enabling the question schedules.
  Applications handling and securing that patient specific information could only be viewed by authorized personnel.
  Applications handling and securing that feedback were realized in different digital channels such as Internet and SMS.

Patient-specific feedback information (see FIG. 5). Some of the characteristics:
  Developed based on the specific aspects of the PP and the patient category.
  Patient specific graphs based upon the collected answers from the patients to the set of questions. This type of feedback was given to the patients in the studies concerning diabetes and atopic dermatitis, not in GAD. In all three studies health care personnel had access to these patient specific graphs, which they used for giving feedback in different ways to their patients.
  The graphs were constructed in a way where relevant variables were matched together and plotted over time according to the set of functions. This showed interesting and valuable relationships and correlations that gave both the patients and/or the healthcare personnel a better understanding of the patients' situation and development.
  Patient specific SMS sent to the patients regarding their treatment and situation (all studies).
  Patient specific SMS sent to the patients with reminders to continue answering questions when their adherence to answer the questions decreased or stopped (all studies).
  Oral communication between health care personnel and the patients based on the patient specific feedback information generated by the CPP (all studies).

Development of the Used QFM

Figure 6:
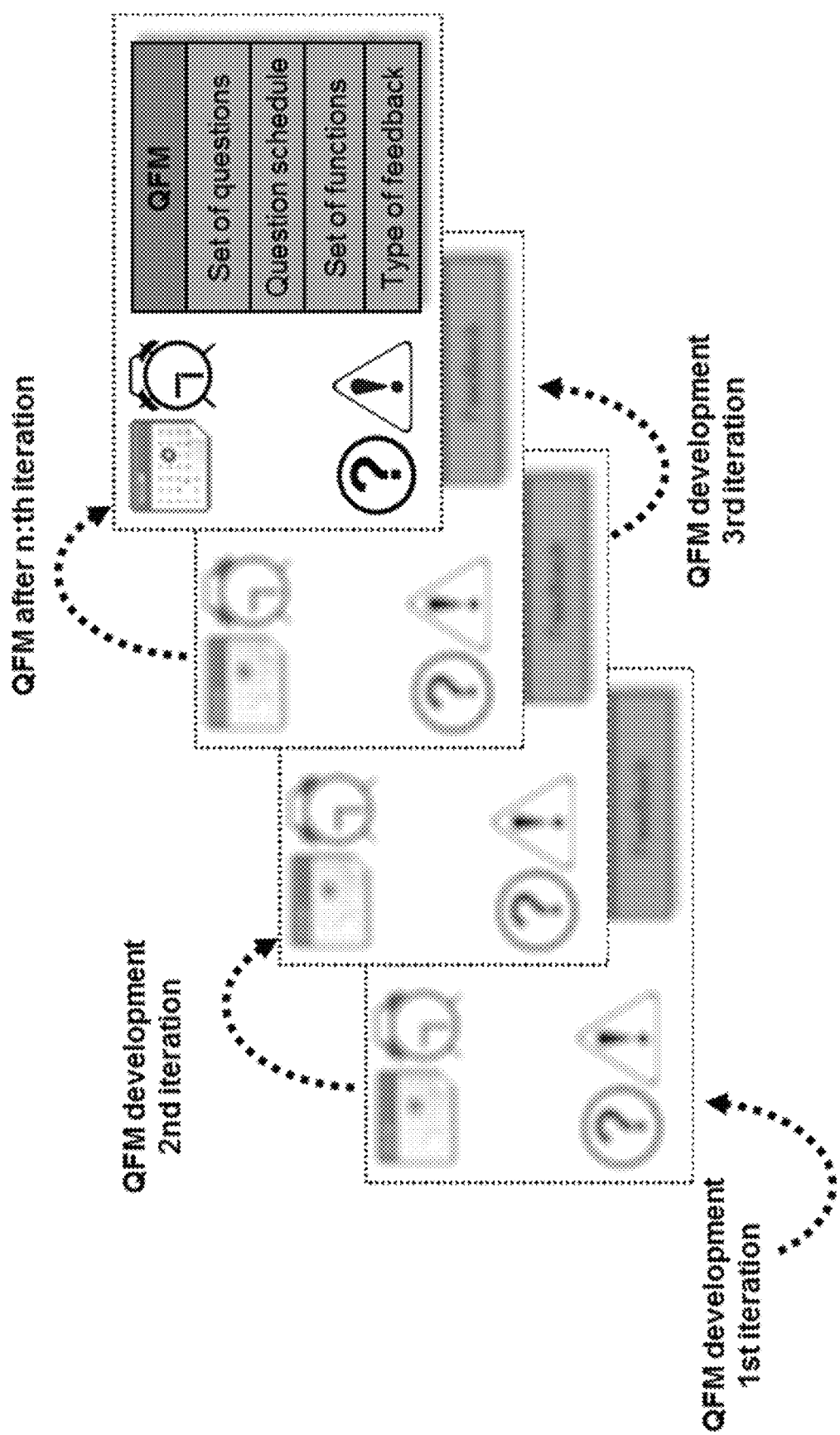
FIG. 6 shows a schematic view of the development of a Question-Feedback model (QFM).
Figure 7:
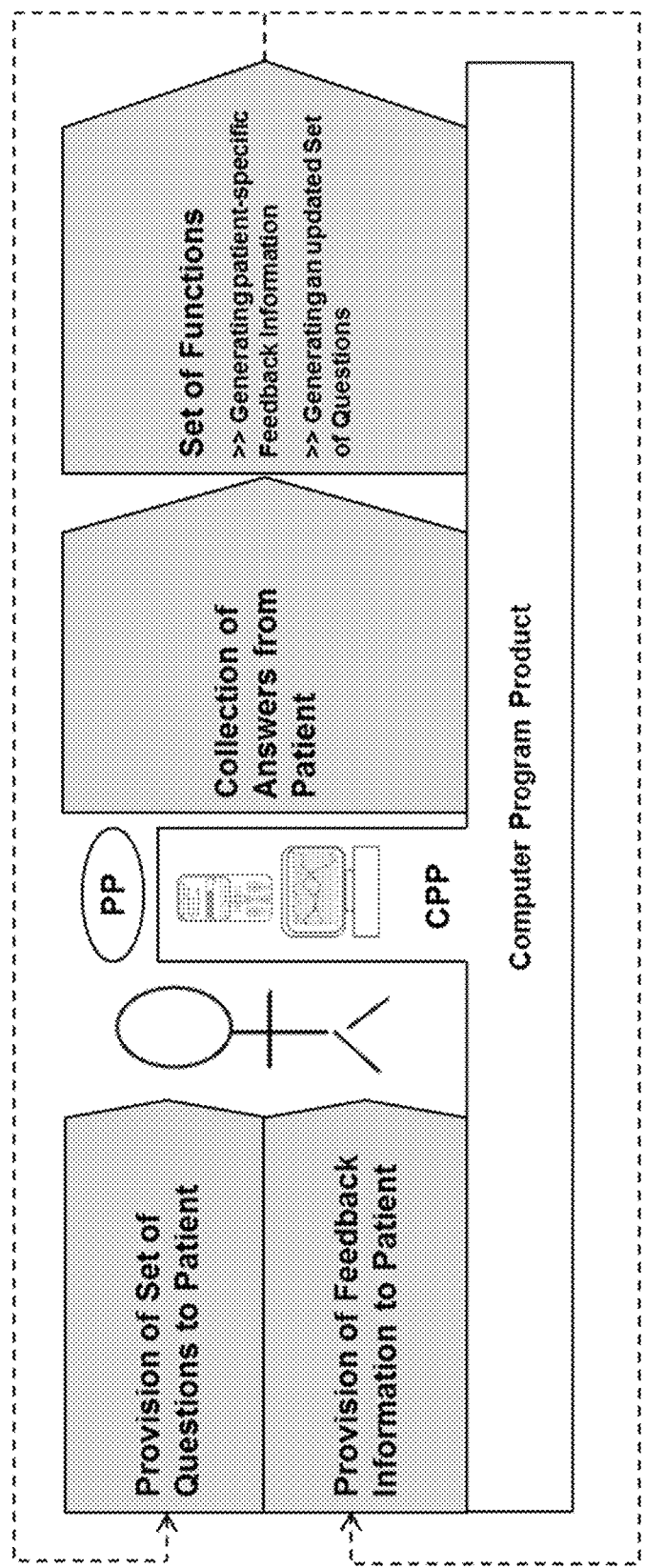
FIG. 7 shows an overview embodiment of QFM in the three first studies in the examples.
Figure 8:
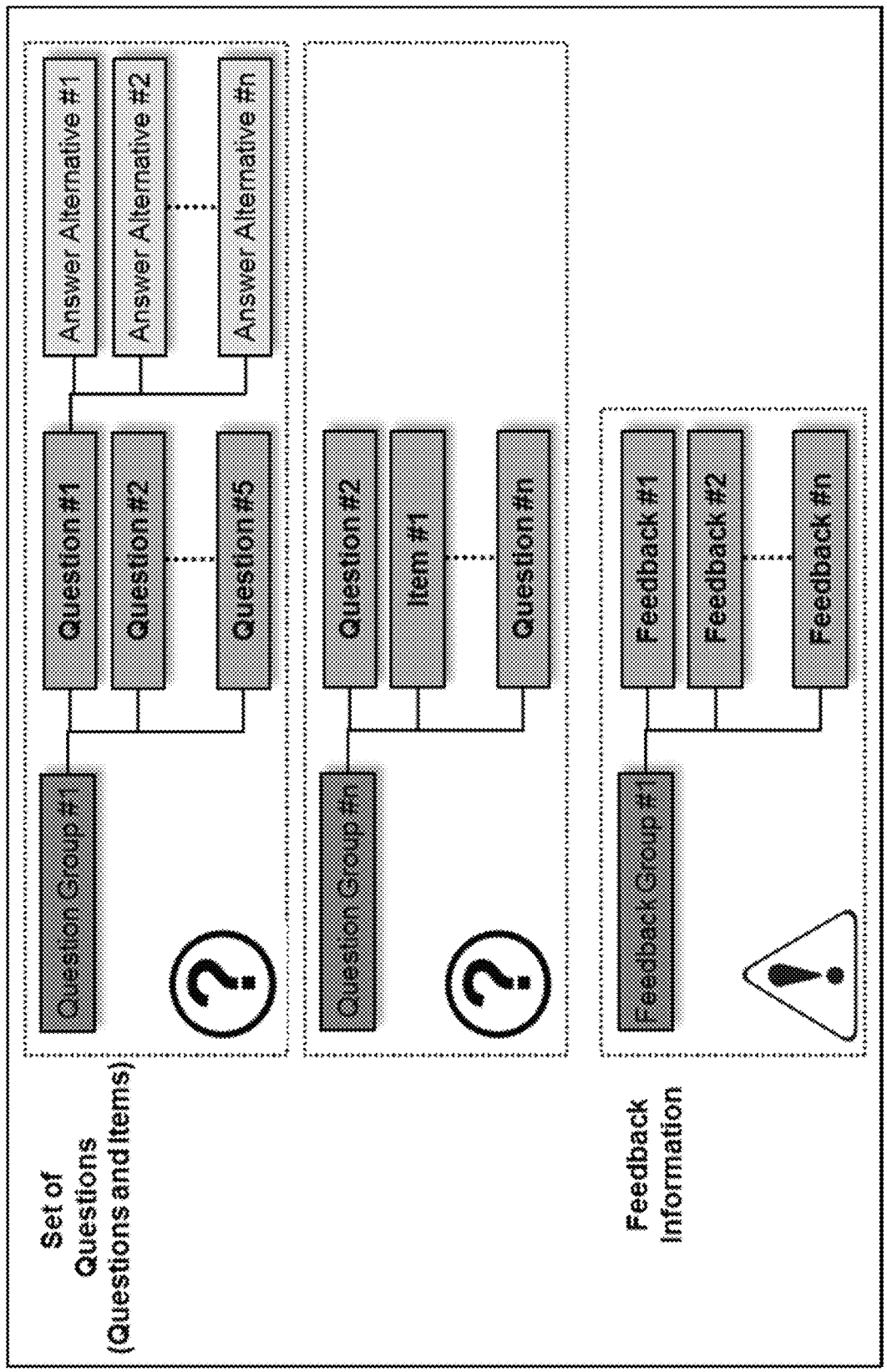
FIG. 8 shows a schematic view of Set of Questions and Feedback Information.
Figure 9:
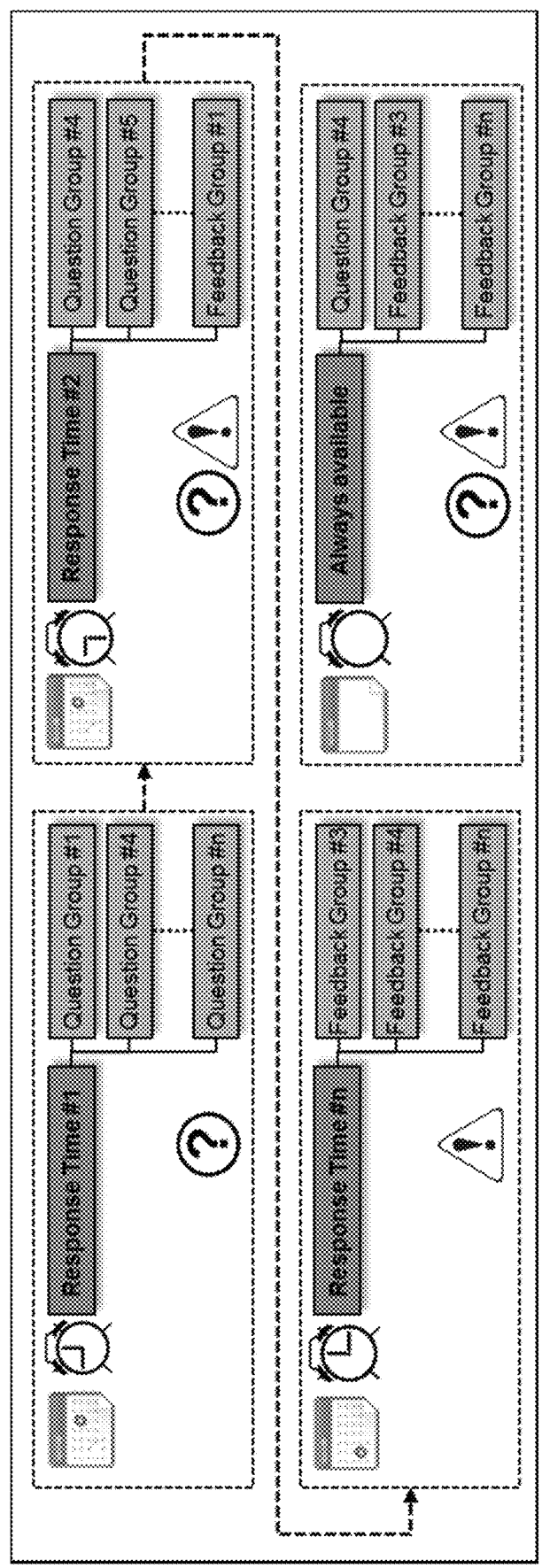
FIG. 9 shows a schematic view of a question schedule.

The development of the used QFM for each of the three pharmaceutical products in the three studies included mainly the steps described earlier in the detailed description and clinically relevant information of the specific pharmaceutical products. Normally it is an iterative process (see FIG. 6) before an optimal QFM for the specific PP (see FIG. 7) has been developed with the set of questions and feedback information (see FIG. 8) and the question schedule (see FIG. 9). As said earlier in the detailed description, many aspects and considerations need to be taken into account when developing a specific QFM.

Overview Technical Implementation of the CPP

Figure 10:
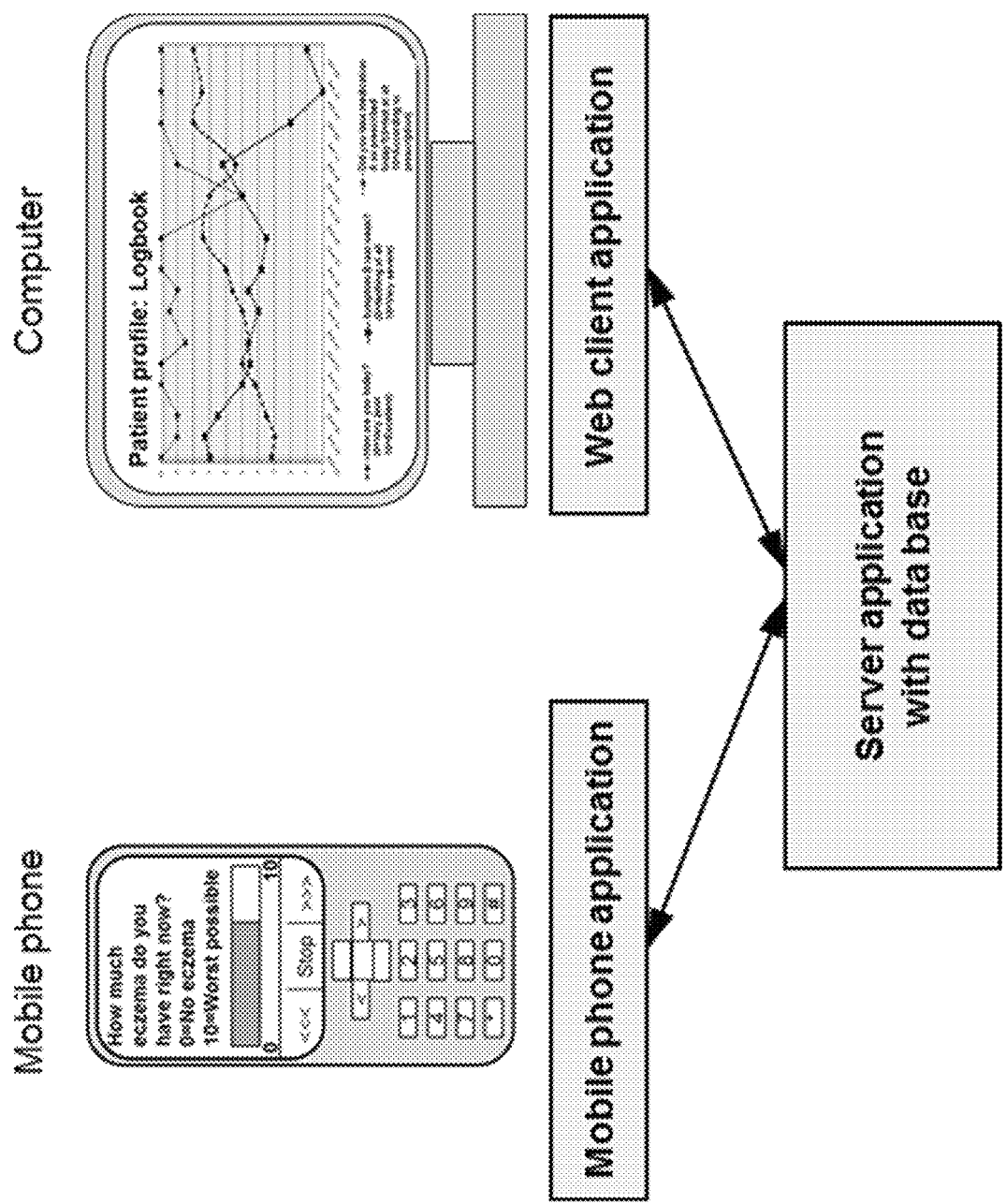
FIG. 10 shows an overview of a technical implementation of the computer program product.

The technical realization and implementation of the CPP in the three studies is illustrated in FIG. 10. The patients were first registered in the system by the health care personnel and after that the patients could download, via mobile internet, the mobile phone application to their mobile phones. The mobile phone application could process, handle and present the questions and answers to the patient. The CPP also consisted of a web client application which was the primary user interface for the health care personnel. A server application with a data base was also an integral part of the implementation of the CPP.

Study 1. Rapid-Acting insulin and Type 1 Diabetes

Background

Type 1 diabetes is an auto-immune disease in which the body's immune system destroys the insulin-producing beta cells in the pancreas. This type of diabetes, also known as juvenile-onset or insulin-dependent diabetes, accounts for 10-15% of all people with the disease. People with type 1 diabetes must inject themselves with insulin several times a day and follow a careful diet and exercise plan.

Glycated hemoglobin (hemoglobin A1c, HbA1c, A1C) is a form of hemoglobin that is measured primarily to identify the average plasma glucose concentration over prolonged periods of time. This serves as a marker for average blood glucose levels over the previous months prior to the measurement.

HbA1c is recommended by WHO (World Health Organization) as a test to diagnose diabetes. The American Diabetes Association recommends that the HbA1c should be below 53 mmol/mol (7.0%) for most patients.

Rapid-acting insulin begins working very quickly inside the body—usually within 5 and 10 minutes. This type of insulin should be taken just before or just after eating. It operates at maximum strength for one to two hours and duration is typically up to four hours. Rapid-acting insulin's are very convenient because they allow diabetic patients to inject themselves, at the time, when they eat.

Study Objectives

The study objective was to evaluate the clinical effect of using the combination product in type 1 diabetes in comparison of using only a PP. The measured variable was HbA1c. The variable was measured directly before the patients entered into the study and directly afterwards when they had concluded their participation.

Primary variable: HbA1c.

Study Design and Set-Up

Two patients were given the combination product, A+B. Both patients had during a longer period of time (more than 6 months) prior to the study been given the specific PP, i.e. only "A", without any significant improvement in the levels of HbA1c.

Length of study: 3 months

Number of patients: 2

Inclusion criteria: Diagnosed diabetes type 1 with more than 58 mmol/mol HbA1c. Access to a mobile phone capable of handling the used CPP.

Study set up: A+B versus A. Two patients used A+B. Evaluation of change in HbA1c, before and after the study.

Used PP: Rapid-acting insulin

The used set of questions can be seen in table 2. The different questions were grouped together in questions groups with corresponding response times (see table 3). Some of the questions were asked three times a week, some more seldom, and some were "spontaneous", i.e., always available for the patient to answer. The question regime, appeared to the patient, could be another than the one presented in the table.

TABLE 2

Questions

| Question | Question type and answer alternatives |
|---|---|
| "Have you been irritated at someone/something today?" | VAS 0-10<br>0 = Not at all irritated,<br>10 = Extremely irritated |
| "How focused are you at school/work?" | VAS 0-10<br>0 = Not at all focused,<br>10 = Very focused |
| "How did you sleep last night?" | VAS 0-10<br>0 = Very poorly, 10 = Very well |
| "For how long time have you exercised today?" | Multiple choice: 0 min, 1-20 min, 21-40 min, 41-60 min, More than 60 min |

TABLE 2-continued

Questions

| Question | Question type and answer alternatives |
|---|---|
| "How many blood glucose levels have you checked today?" | Numeric |
| "How many units of rapid-acting insulin did you take at breakfast?" | Numeric |
| "How many units of rapid-acting insulin did you take at the meal?" | Numeric |
| "When did you eat breakfast?" | Multiple choice: Before 6 am, Between 6-8 am, Between 8-10 am, I didn't eat breakfast |
| "When did you eat lunch?" | Multiple choice: Before 11 am, Between 11 am-1 pm, Between 1-3 pm, I didn't eat lunch |
| "What was your blood glucose level approximately 1.5 hours after breakfast (mmol/l)?" | Numeric |
| "What was your blood glucose level approximately 1.5 hours after lunch (mmol/l)?" | Numeric |
| "What was your blood glucose level before breakfast (mmol/l)?" | Numeric |
| "What was your blood glucose level before lunch (mmol/l)?" | Numeric |
| "How hard is it to have been diagnosed with type 1 diabetes?" | VAS 0-10<br>0 = Not at all difficult,<br>10 = Extremely hard |
| "To what extent has diabetes affected your activities during the week?" | VAS 0-10<br>0 = Very much, 10 = Not at all |

TABLE 3

Question schedule

| Question group | Response time (alerts from CPP) |
|---|---|
| "Morning questions" | Mondays, Wednesdays, and Fridays at 10 am |
| "Afternoon questions" | Mondays, Wednesdays, and Fridays at 3 pm |
| "Weekly questions" | Once a week on Fridays at 3 pm |
| "Monthly questions" | Once a month on Fridays at 3 pm |
| "Spontaneous questions" | Questions always available to answer |

Type of Feedback

The feedback to the patients was crucial in order to achieve a positive clinical effect of the combination product.

Figure 11:
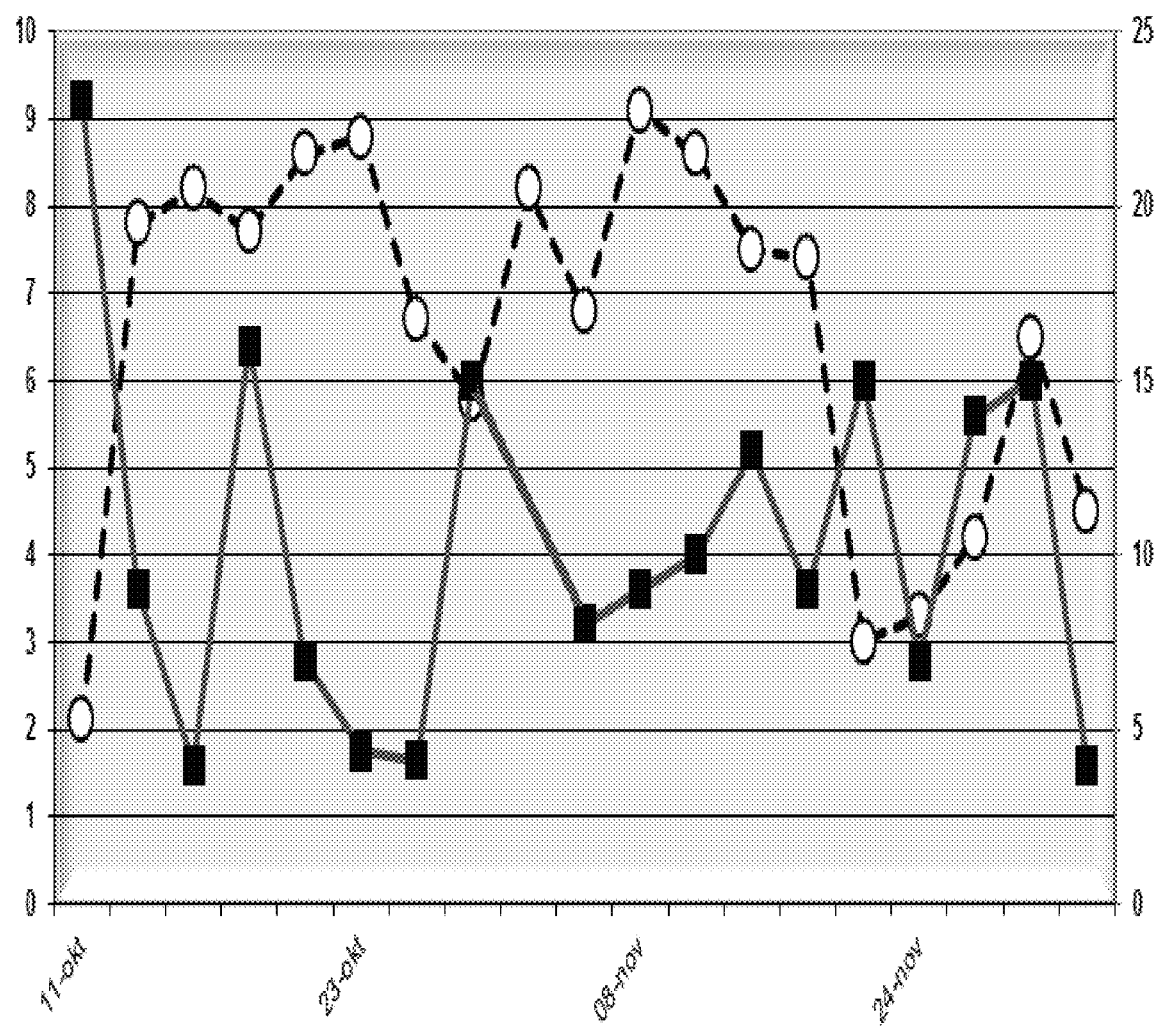
FIG. 11 shows an illustrative example of one of the patient's feedback graphs from study 1 in the examples.

Both the healthcare personnel and the patients had access to updated graphs with the patient's specific feedback information based on the collected answers. The graphs were constructed in a way where relevant variables were matched together and plotted over time, examples of the matched variables are shown in table 4. An illustrative example with one of the patient's feedback graphs is shown in FIG. 11. Examples of given feedbacks to patients were the following text messages (SMS) sent via the CP, see table 5.

TABLE 4

Examples of grouping of variables in feedback graphs

| Grouping of feedback graphs | Questions/Variables |
|---|---|
| Blood glucose and insulin at breakfast | "What was your blood glucose level before breakfast (mmol/l)?"<br>"How many units of rapid-acting insulin did you take at breakfast?"<br>"What was your blood glucose level approximately 1.5 hours after breakfast (mmol/l)?" |

TABLE 4-continued

Examples of grouping of variables in feedback graphs

| Grouping of feedback graphs | Questions/Variables |
|---|---|
| Sleep and blood glucose | "How did you sleep last night?" "What was your blood glucose level before breakfast (mmol/l)?" |

TABLE 5

Illustrative examples of feedback messages

| Patient | Number of SMS-messages | Examples of SMS-messages from health care personnel | Examples of SMS message generated from the CPP |
|---|---|---|---|
| Patient 1 | 10 from health care personnel 3 automatically generated from the CPP | "Hi, it would be interesting and valuable to see more test values, continuously. Please record more blood glucose readings after breakfast and lunch." "Hi, enjoy spring break, but don't forget to check your blood glucose levels" | "Don't forget to answer the questions continuously. If you haven't received alerts from your mobile phone recently, please try to restart the application again." |
| Patient 2 | 9 from health care personnel 2 automatically generated from the CPP | "Hi, don't forget to record your blood glucose values 1.5 hours after breakfast and lunch. These readings are important." "Good work! But I miss some blood glucose readings after your meals" | |

Study Results

The result of the study is presented in the table 6 below.

TABLE 6

Study results

| Patient | HbA1c before enrollment | HbA1c after completion | Change in HbA1c |
|---|---|---|---|
| Patient 1 | 106 mmol/mol | 89 mmol/mol | −17 mmol/mol |
| Patient 2 | 80 mmol/mol | 63 mmol/mol | −17 mmol/mol |

The result shows a substantial improvement in the clinical effect of the combination product, A+B, in comparison to only A. The value of the primary variable HbA1c improved significantly, 19% as an average, when the patients had been using the combination product, A+B compared to before the study when they were using only A during at least 6 months. The period of using only A for the patients resulted in the level of HbA1c measured before enrollment into the study.

The result of the study indicates a significant clinical effect of the invention, the combination product.

Study 2. Takrolimus and Atopic Dermatitis

Background

Atopic dermatitis is an inflammatory, chronically relapsing, non-contagious and pruritic skin disorder. Although there is no cure for atopic eczema, and its cause is not well understood, it can be treated very effectively in the short term through a combination of prevention (learning what triggers the skin reactions) and drug therapy.

Protopic Ointment (active substance takrolimus) is a prescription ointment used to treat moderate to severe eczema. Protopic is for use after other prescription medicines have not worked or when a doctor recommends that other prescription medicines should not be used. Protopic should be used for short periods, and, if needed, treatment may be repeated with breaks in between.

Study Objectives

The study objectives were twofold:
1. Evaluate the possible improvements in clinical effect of using the combination product, A+B compared to B.
   Measured symptoms: Perceived level of eczema and perceived level of itching.
2. Evaluate the possible perceived clinical effect in the value of the combination product.
   Measured variable: Perceived level of practical value of the combination product.

Study Design and Set-Up

Four patients were given the combination product, A+B, and one patient the CPP, just B. Prior to entering into the study none of the patients had used either the PP or the CPP.

Length of study: 3 months.

Number of patients: 5 in total. Four in the intervention group with A+B, and one in the control group with B.

Inclusion criteria: Diagnosed atopic dermatitis and access to a cellular phone capable of handling the used CPP.

Used PP: Protopic

The one patient in the control group used a cortiscosteroid based regimen instead of Protopic. The patient used the same CPP and QFM as the other patients, but this QFM was adapted to Protopic and not the cortiscosteroid based pharmaceutical product.

Two different study set-ups:
1. Comparison of A+B versus B. Four patients using A+B. Control group with one patient using just B.
2. Evaluation of A+B over time, i.e., start period compared with end period. Four patients using A+B.

The used set of questions can be seen in table 7. The different questions were grouped together in question groups with corresponding response times (see table 8). The questions were asked twice a week and they were also "spontaneous", i.e., always available for the patient to answer.

TABLE 7

Questions

| Question | Question type and answer alternatives |
|---|---|
| "How much eczema do you have right now?" | VAS 0-10 0 = No eczema, 10 = Worst possible |
| "How much itching did you have the last day and night?" | VAS 0-10 0 = Nothing at all, 10 = Very severe |
| "How does the treatment practically work out for you?" | VAS 0-10 0 = Very bad, 10 = Very good |
| "If you have eczema - how often do you anoint yourself with Protopic?" | Multiple choice: Daily, Twice a week, Not at all |
| "If you don't have eczema - how often do you anoint yourself with Protopic?" | Multiple choice: Daily, Twice a week, Not at all |

TABLE 8

Question schedule

| Question group | Response time (alerts from CPP) |
|---|---|
| "Regular questions" | Mondays and Thursdays at 7 pm |
| "Spontaneous questions" | Questions always available to answer |

The type of feedback was, as stated earlier, access to own patient specific graphs, received personal and patient specific SMS, and feedback from the health care personnel via oral communication.

Measured Variables

The measured variables (see table 9) are symptom levels which are perceived estimates by each patient at every measure point. The levels of symptoms at the beginning of the study are compared to the levels of the symptoms at the end of the study. In parallel with the study, all patients were answering a continuous follow-up question regarding the perceived value of practical functioning of using the combination product, i.e. the medical treatment combined with the computerized program.

TABLE 9

Measured variables

| Symptom/Variable | Question in QFM | Question type |
|---|---|---|
| Eczema | "How much eczema do you have right now?" | VAS 0-10<br>0 = No eczema,<br>10 = Worst possible |
| Itching | "How much itching did you have the last day and night?" | VAS 0-10<br>0 = Nothing at all,<br>10 = Very severe |
| Practical functioning of treatment | "How does the treatment practically work out for you?" | VAS 0-10<br>0 = Very bad,<br>10 = Very good |

| Measured variable | Definition | Data type |
|---|---|---|
| Eczema (average) | Average for symptom during the period | 0-10<br>0 = No eczema,<br>10 = Worst possible |
| Itching (average) | Average for symptom during the period | 0-10<br>0 = Nothing at all,<br>10 = Very severe |
| Practical functioning of treatment (average) | Average for variable during the period | 0-10<br>0 = Very bad,<br>10 = Very good |

Type of Feedback

The feedback to the patients was crucial in order to achieve a positive clinical effect of the combination product.

Figure 12:
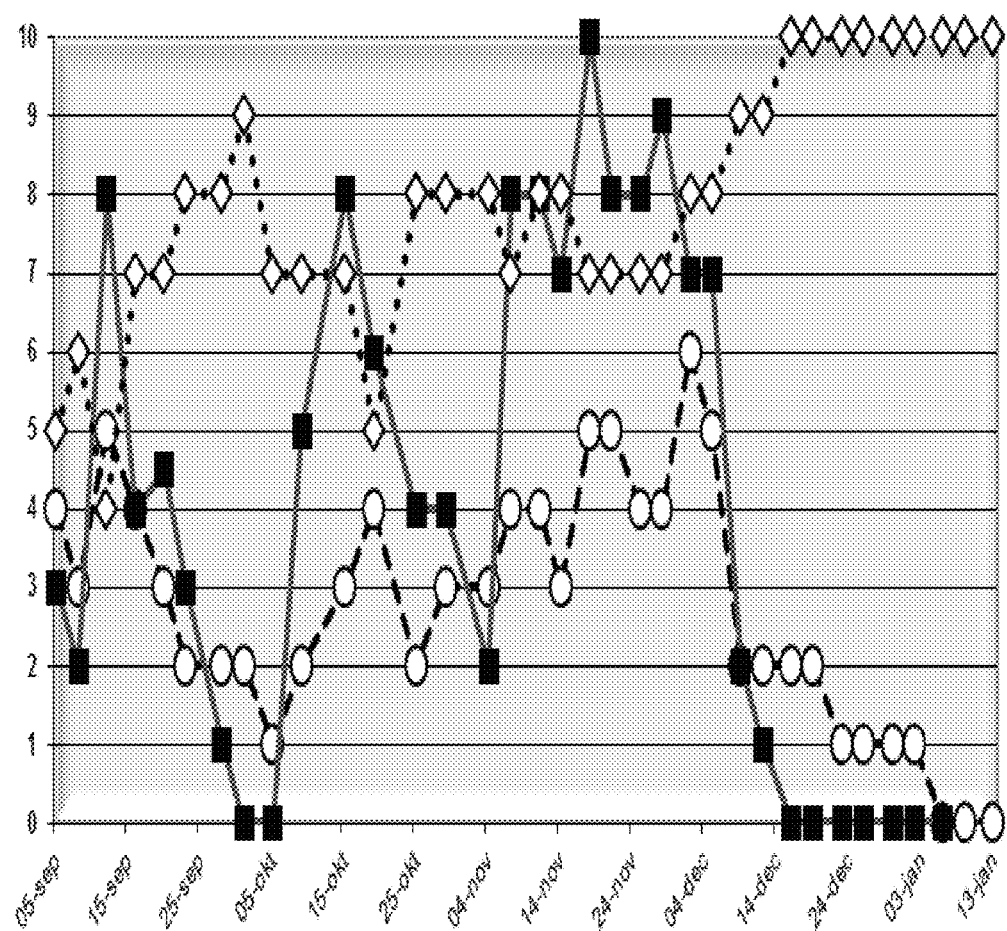
FIG. 12 shows an illustrative example of one of the patient's feedback graphs from study 2 in the examples.

Both the healthcare personnel and the patients had access to updated graphs with the patient's own specific feedback information based on the collected answers. The graphs were constructed in a way where relevant variables were matched together and plotted over time, examples of the matched variables are shown in table 10. An illustrative example with one of the patient's feedback graphs is shown in FIG. 12. Examples of given feedbacks to patients, and subsequent actions and clinical effects, are the following text messages (SMS) sent via the CPP, to two of the patients can be seen in table 11.

TABLE 10

Example of grouping of variables in feedback graphs

| Grouping of feedback graphs | Questions/Variables |
|---|---|
| Eczema, itching, and practical treatment | "How much eczema do you have right now?"<br>"How much itching did you have the last day and night?"<br>"How does the treatment practically work out for you?" |
| Eczema and adherence Protopic | "How much eczema do you have right now?"<br>"If you have eczema - how often do you anoint yourself with Protopic?"<br>"If you don't have eczema - how often do you anoint yourself with Protopic?" |

TABLE 11

Illustrative examples of feedback messages

| Feedback | Patient reaction to feedback | Result of reaction to feedback |
|---|---|---|
| "You have pretty much itching and eczema. Try to instead use the PP on a daily basis for a couple of weeks." | The patient started using the PP on a daily basis at once. | The measured variables itching and eczema started to improve. |
| "Your eczema and itching seem to be in decent control. If you have any question please get in contact." | From that date the patient was fully adherent to the PP. | The measured variables remained on a stable and very positive level. |

Study Results

The study results, measured variables and changes, are presented in the table 12 below. Decimal rounding has been made to the data in the table. N/A=Not applicable.

TABLE 12

Study results

| Patient | Type | Eczema Start period | Eczema End period | Eczema Change | Itching Start period | Itching End period | Itching Change | Practical treatment Start period | Practical treatment End period | Practical treatment Change |
|---|---|---|---|---|---|---|---|---|---|---|
| Patient 1 | A + B | 2.7 | 2.5 | −0.2 | 2.1 | 2.1 | 0.0 | 9.3 | 10 | 0.7 |
| Patient 2 | A + B | 2.8 | 0.2 | −2.6 | 3.3 | 0.0 | −3.3 | 6.6 | 10 | 3.4 |
| Patient 3 | A + B | 5.3 | 4.3 | −1.0 | 5.6 | 5.0 | −0.6 | 4.3 | 5.3 | 1.0 |
| Patient 4 | A + B | 6.4 | 5.1 | −1.2 | 6.6 | 6.0 | −0.6 | 6.4 | 7.9 | 1.6 |
| Patient 5 | B | 2.3 | 4.6 | 2.2 | 2.8 | 4.9 | 2.0 | N/A | N/A | N/A |

The result shows a significant improvement in the clinical effect of the combination product, A+B compared to B, see table 12. The level of clinical effect, concerning both the perceived levels of eczema and itching, is improving substantially; see the columns Eczema Change and Itching Change in the table above. Both measured symptoms are significantly decreasing, both in comparison with the initial values and with the progress of the control group.

The result shows also a significant improvement in perceived value of practical functionality of using the combination product over time.

Aspects Comparing A+B Versus B

The patient in the control group shows a negative result in both perceived level of eczema and itching. This result is an effect of the QFM being adapted for the specific PP. The actual patient in the control group is not using the specific PP, implying a situation where the actual QFM not being optimal for the specific patient. In order to achieve an effect of the invention, the QFM has to be adapted to the specific PP and to the specific situation for the actual patient. None of this is the case for the patient in the control group in this study.

Aspects Evaluating A+B Over Time

The patient's adherence to the whole treatment, i.e. the combination product A+B, is measured by asking how the patient perceives the practical functioning of the treatment. A major reason for that is that the usage of the PP, from a patient perspective, is done through a cumbersome procedure From an invention perspective, the result that the perceived value is increasing over time is positive due to the following aspects:

The value of the CPP should, according to the insights behind the invention, increase over time, because it takes some time for a patient to get the full value of the QFM and the invention.

The measured variable is related to a perceived quality of life of the patient, implying that such a factor might also develop positively.

The adherence and sense of practical functioning using only a PP is normally long-term constant or decreasing.

After the study the patients asked for even more frequent feedback. They felt a value in receiving feedback about their situation and how to act in order to improve their health situation. They also wanted the set of questions even more adapted to their own specific situation as a group of patients and to the specific PP. They also wanted to have furthermore individualized questionnaires. This kind of comments supports the idea behind the invention regarding the importance of personalized feedback, and also shows that the development of the QFM is crucial in order to optimize the clinical effect.

Study 3. Pregabalin and Generalized Anxiety Disorder (GAD)

Background*

*Source: European Medicines Agency, Summary of the European Public Assessment Report (EPAR) for Lyrica.

Generalized anxiety disorder (GAD) is an anxiety disorder. The symptoms of GAD are prolonged excessive anxiety and worry that are difficult to control. GAD can also cause restlessness or feeling keyed up or on edge, being easily fatigued (tired), having difficulty concentrating or mind going blank, feeling irritable, having muscle tension or sleep disturbance. This is different to the stresses and strains of everyday life.

Lyrica is a medicine that contains the active substance pregabalin. Lyrica is used to treat adults with the following conditions: GAD, neuropathic pain, or epilepsy. Lyrica is available in 25, 50, 75, 100, 150, 200, 225, and 300 mg capsules. The medicine can only be obtained with a prescription.

The recommended starting dose of Lyrica is 150 mg per day, divided into two or three doses. After three to seven days, the dose can be increased to 300 mg per day. Doses can be increased up to twice more until the most effective dose is reached. The maximum dose is 600 mg per day. Stopping treatment with Lyrica should also be done gradually, over at least a week.

Like all medicines, Lyrica can have side effects, although not everyone gets them.

Very common side-effects which may affect more than 1 person in 10 are: dizziness, tiredness.

Common side-effects which may affect more than 1 person in 100 are among others: dry mouth, nausea Study Objectives There were four study objectives (see table 13).

TABLE 13

Study objectives

| Study objective | Measured variable(s) | |
|---|---|---|
| 1. Evaluate the possibility to improve clinical effect of the combination product versus PP. | Symptoms: Anxiety daytime, Anxiety evening/night, Fatigue, Muscle tension daytime, and Muscle tension evening/night | Side effects: Dizziness, Nausea, and Dry mouth |
| 2. Evaluate the possibility to improve patient safety of the combination product versus PP. | Symptoms: Anxiety daytime, Anxiety evening/night, Fatigue, Muscle tension daytime, and Muscle tension evening/night | Side effects: Dizziness, Nausea and Dry mouth |
| 3. Evaluate the possibility to improve the patients' perceived Quality of Life when using the combination product. | Primary variable: Perceived Quality of Life | |
| 4. Evaluate the adherence to the PP. | Primary variable: The reported intake of the PP | |

Study Design and Set-Up

Three patients participated in the study, where two of them were given the combination product, A+B, and the third was given the PP, A. All three patients were using an evaluation tool in order to capture the continuous data concerning their current health situation. Prior to entering the study none of the patients had used either the PP or the CPP.

Length of study: 2 months.

Number of patients: 3

Inclusion criteria: Diagnosed GAD and access to a cellular phone capable of handling the used CPP.

Used PP: Lyrica

The two patients using the combination product were evaluated against the one patient using only the PP and being treated according to ordinary health care in Sweden. In the ordinary health care the benefits from the combination product was not possible to utilize because it was not implemented there.

The study consisted of three study set-ups (see table 14).

TABLE 14

Study set-ups GAD

| Study set-up | Evaluation | Patients |
|---|---|---|
| 1 | A + B in detailed patient outcome comparison with A | A + B: Patient 1 vs A: Patient 3 |
| 2 | A + B in detailed patient outcome comparison with A | A + B: Patient 2 vs A: Patient 3 |
| 3 | A + B in comparison to other study results | A + B: Patient 1 and 2 vs Results from published scientific studies |

Due to the specific and profound study objectives, detailed outcome and behavior during the study period from the patients were evaluated against each other. The measurements of the patient outcomes were evaluated for each patient in different time phases during the treatment period.

In order to measure the appropriate patient outcome, the patients were continuously followed-up. In this sense, patient 3 also had a similar set of questions, which the patient answered to. The used QFM for the patients in the intervention group, patient 1 and 2:

1. Set of questions.
2. Set of functions generating individual and patient specific feedback information.
3. Feedback based upon the individual patient specific feedback information.

The used set of questions for the patient in the control group, patient 3:

1. Set of questions similar to the intervention group in order to capture patient reported outcome data
2. No set of functions.
3. No feedback information or feedback.

The used set of questions can be seen in table 15. The different questions were grouped together in questions groups with corresponding response times (see table 16) creating the question schedule. Some of the questions were asked daily, some weekly, and some were "spontaneous", i.e., always available for the patient to answer.

TABLE 15

Questions

| Question | Question type and answer alternatives |
|---|---|
| "Are you anxious right now?" | VAS 0-10 |
| "Have you been anxious today?" | 0 = Not at all, |
| "Have you been anxious during evening/night?" | 10 = Extremely anxious |
| "Have you been tired today?" | VAS 0-10 |
|  | 0 = Not at all, |
|  | 10 = Extremely tired |
| "Have you felt muscle tension today?" | VAS 0-10 |
| "Have you felt muscle tension during evening/night?" | 0 = Not at all, 10 = Extreme muscle tension |
| "Have you felt any dizziness today?" | Multiple choice: Yes/No |
| "Have you felt any dizziness during evening/night?" | |
| "Have you felt any nausea today?" | Multiple choice: Yes/No |
| "Have you felt any nausea during evening/night?" | |
| "Have you felt any mouth dryness today?" | Multiple choice: Yes/No |
| "Have you felt any mouth dryness during evening/night?" | |

TABLE 15-continued

Questions

| Question | Question type and answer alternatives |
|---|---|
| "How is your health related Quality of Life?" | VAS 0-10 0 = Extremely bad Quality of Life, 10 = Extremely good Quality of Life |
| "Have you been able to perform everyday activities today?" | Multiple choice: Yes/No |
| "Have you exercised today?" | VAS 0-10 |
| "Have you exercised this week?" | 0 = Not at all, 10 = Exercised extremely |
| "When did you take your morning dose of PP?" | Multiple choice: Before 7 am, 7-8 am, 8-9 am, After 9 am, No morning dose |
| "When did you take your evening dose of PP yesterday?" | Multiple choice: Before 6 pm, 6-7 pm, 7-8 pm, After 8 pm, No evening dose |
| "What dose of PP did you take this morning?" | Multiple choice: 75 mg or lower, 100-175 mg, 200-275 mg, 300 mg, No morning dose |
| "What dose of PP did you take yesterday evening?" | Multiple choice: 75 mg or lower, 100-175 mg, 200-275 mg, 300 mg, No evening dose |
| "What is your current daily dose of PP?" | Numeric |
| "What is your current weight?" | Numeric |

TABLE 16

Question schedule

| Question group | Response time (alerts from CPP) |
|---|---|
| "Daily morning questions" | Daily at 10 am |
| "Daily evening questions" | Daily at 8 pm |
| "Weekly questions" | Once a week on Sundays at 8 pm |
| "Spontaneous questions" | Questions always available to answer |

Type of Feedback

The type of feedback was, as stated earlier, received personal and patient specific SMS, and feedback from the health care personnel via oral communication.

The healthcare personnel had access to updated graphs with the patient's specific feedback information based on the collected answers and the set of functions. The graphs were constructed in a way where relevant variables concerning the PP were matched together and plotted over time, examples of the matched variables are shown in table 17. An illustrative example with one of the patient's feedback graphs is shown in graph 3. Examples of given feedbacks to patients 1 and 2 were the following text messages (SMS) sent via the CPP (table 18).

TABLE 17

Example of grouping of variables in feedback graphs

| Grouping of feedback graphs | Question/Variable |
|---|---|
| Clinical effect and adherence Lyrica | "Have you been anxious today?" |
| | "Have you been tired today?" |
| | "What is your current daily dose of PP?" |
| | "What dose of PP did you take yesterday evening?" |
| | "What dose of PP did you take this morning?" |
| Side effects daytime and adherence Lyrica | "Have you felt any dizziness today?" |
| | "Have you felt any mouth dryness today?" |
| | "Have you felt any nausea today?" |
| | "What is your current daily dose of PP?" |
| | "What dose of PP did you take yesterday evening?" |
| | "What dose of PP did you take this morning?" |

TABLE 17-continued

Example of grouping of variables in feedback graphs

| Grouping of feedback graphs | Question/Variable |
|---|---|
| Side effects evening/ night and adherence Lyrica | "Have you felt any dizziness during evening/night?" "Have you felt any mouth dryness during evening/night"?" "Have you felt any nausea during evening/night?" "What is your current daily dose of PP?" "What dose of PP did you take yesterday evening?" "What dose of PP did you take this morning?" |
| Exercise, muscle tension, and fatigue | "Have you exercised today?" "Have you felt muscle tension today?" "Have you been tired today?" |

TABLE 18

Illustrative examples of feedback messages

| Patient | Number of SMS-messages | Examples of SMS message generated from the CPP |
|---|---|---|
| Patient 1 | 4 automatically generated from the CPP | "Don't forget to answer the questions continuously. If you haven't received alerts from your mobile phone recently, please try to restart the application again." |
| Patient 2 | 2 automatically generated from the CPP | |

Measured Variables

The measured variables (see table 19) were symptom and side effect levels which were perceived estimates by each patient at every measure point. The change in levels of symptoms and side effects between different measured times were used for comparisons. Symptoms and side effects are many times closely related in GAD. In this study anxiety, fatigue, and muscle tension were defined as symptoms while dizziness, nausea, and dry mouth were considered as side effects. This study focused on the overall clinical effect and patient safety aspects therefore it was not crucial to the results if a measured variable could have been defined differently.

TABLE 19

Measured variables

| Symptom/ Variable | Question in QFM | Question type |
|---|---|---|
| Anxiety | "Have you been anxious today?" "Have you been anxious during evening/night?" | VAS 0-10 0 = Not at all, 10 = Extremely anxious |
| Fatigue | "Have you been tired today?" | VAS 0-10 0 = Not at all, 10 = Extremely tired |
| Muscle tension | "Have you felt muscle tension today?" "Have you felt muscle tension during evening/night?" | VAS 0-10 0 = Not at all, 10 = Extreme muscle tension |
| Dizziness | "Have you felt any dizziness today?" "Have you felt any dizziness during evening/night?" | Multiple choice: Yes/No |
| Nausea | "Have you felt any nausea today?" "Have you felt any nausea during evening/night?" | Multiple choice: Yes/No |
| Dry mouth | "Have you felt any mouth dryness today?" "Have you felt any mouth dryness during evening/night"?" | Multiple choice: Yes/No |
| Health related Quality of Life | "How is your health related quality of life?" | VAS 0-10 0 = Extremely bad quality of life, 10 = Extremely good quality of life |

| Measured variable | Definition | Data type |
|---|---|---|
| Anxiety daytime (average) | Average for variable during the period | 0-10 0 = Not at all, 10 = Extremely anxious |
| Anxiety evening/night (average) | Average for variable during the period | 0-10 0 = Not at all, 10 = Extremely anxious |
| Fatigue (average) | Average for variable during the period | 0-10 0 = Not at all, 10 = Extremely tired |
| Muscle tension daytime (average) | Average for variable during the period | 0-10 0 = Not at all, 10 = Extreme muscle tension |
| Muscle tension evening/night (average) | Average for variable during the period | 0-10 0 = Not at all, 10 = Extreme muscle tension |
| Dizziness (frequency) | Frequency of Yes answers for the two questions about dizziness during the period | 0-100% |
| Nausea (frequency) | Frequency of Yes answers for the two questions about nausea during the period | 0-100% |
| Dry mouth (frequency) | Frequency of Yes answers for the two questions about mouth dryness during the period | 0-100% |
| Health related Quality of Life (average) | Average for variable during the period | 0-10 0 = Extremely bad quality of life, 10 = Extremely good quality of life |

Study Results

The study results, measured variables and changes, are presented in the tables 20-22 below. Decimal rounding has been made to the data in the table. p.p.=percentage points. N/A=not applicable.

TABLE 20

Study results patient 1

| Phase/Period | Type | Measured variable | Anxiety Daytime | Anxiety Evening/Night | Fatigue | Muscle tension Daytime | Muscle tension Evening/Night | Dizziness | Nausea | Dry mouth | Quality of Life |
|---|---|---|---|---|---|---|---|---|---|---|---|
| 1st phase | A + B | Average value phase | 4.1 | 3.6 | 5.2 | 0.9 | 0.6 | 7% | 14% | 98% | N/A |
| 2nd phase | A + B | Average value phase | 4.8 | 3.8 | 2.0 | 0.0 | 0.0 | 0% | 11% | 100% | N/A |
| | | Change 2nd vs 1st phase | 0.6 | 0.2 | −3.2 | −0.9 | −0.6 | −7 p.p. | −3 p.p. | 2 p.p. | N/A |
| 3rd phase | A + B | Average value phase | 3.0 | 1.3 | 1.6 | 0.0 | 0.0 | 0% | 0% | 47% | N/A |
| | | Change 3rd vs 2nd phase | −1.8 | −2.5 | −0.4 | 0.0 | 0.0 | 0 | −11 p.p. | −53 p.p. | N/A |
| Start period | A + B | Average value period | 4.8 | 3.8 | 5.7 | 2.1 | 1.1 | 7% | 14% | 98% | 1.0 |
| End period | A + B | Average value period | 3.2 | 1.3 | 1.7 | 0.0 | 0.0 | 0% | 0% | 47% | 2.8 |
| | | Change End vs Start period | −1.6 | −2.5 | −4.0 | −2.1 | −1.1 | −7 p.p. | −14 p.p. | −51 p.p. | 1.8 |

TABLE 21

Study results patient 2

| Phase/Period | Type | Measured variable | Anxiety Daytime | Anxiety Evening/Night | Fatigue | Muscle tension Daytime | Muscle tension Evening/Night | Dizziness | Nausea | Dry mouth | Quality of Life |
|---|---|---|---|---|---|---|---|---|---|---|---|
| 1st phase phase | A + B | Average value | 4.6 | 2.3 | 4.4 | 6.0 | 4.7 | 8% | 22% | 69% | N/A |
| Start period | A + B | Average value period | 4.8 | 4.4 | 5.4 | 7.4 | 8.0 | 13% | 33% | 0% | 5.0 |
| End period | A + B | Average value period | 7.0 | 3.2 | 7.8 | 3.6 | 3.6 | 13% | 40% | 100% | 5.0 |
| | | Change End vs Start period 1st phase | 2.2 | −1.2 | 2.4 | −3.8 | −4.4 | 0 p.p. | 7 p.p. | 100 p.p. | N/A |
| 2nd phase | B | Average value phase | 4.2 | 2.6 | 2.7 | 4.3 | 3.8 | 0% | 14% | 0% | N/A |
| | | Change 2nd phase vs 1st phase | −0.4 | 0.3 | −1.7 | −1.7 | −0.9 | −8 p.p. | −9 p.p. | −69 p.p. | N/A |

TABLE 22

Study results patient 3

| Phase/Period | Type | Measured variable | Anxiety Daytime | Anxiety Evening/Night | Fatigue | Muscle tension Daytime | Muscle tension Evening/Night | Dizziness | Nausea | Dry mouth | Quality of Life |
|---|---|---|---|---|---|---|---|---|---|---|---|
| 1st phase | A | Average value phase | 3.5 | 2.8 | 5.4 | 6.3 | 3.9 | 13% | 38% | 0% | N/A |

TABLE 22-continued

Study results patient 3

| Phase/Period | Type | Measured variable | Anxiety Daytime | Anxiety Evening/Night | Fatigue | Muscle tension Daytime | Muscle tension Evening/Night | Dizziness | Nausea | Dry mouth | Quality of Life |
|---|---|---|---|---|---|---|---|---|---|---|---|
| 2$^{nd}$ phase | A | Average value phase | 3.0 | 2.9 | 5.0 | 7.8 | 7.4 | 0% | 11% | 0% | N/A |
| | | Change 2$^{nd}$ vs 1$^{st}$ phase | −0.5 | 0.1 | −0.4 | 1.5 | 3.5 | −13 p.p. | −27 p.p. | 0 p.p. | N/A |
| 3$^{rd}$ phase | A | Average value phase | 1.9 | 1.8 | 5.1 | 7.1 | 7.2 | 0% | 0% | 0% | N/A |
| | | Change 3$^{rd}$ vs 2$^{nd}$ phase | −1.1 | −1.1 | 0.1 | −0.7 | −0.3 | 0 p.p. | −11 p.p. | 0 p.p. | N/A |
| Start period | A | Average value period | 3.8 | 2.4 | 5.6 | 5.9 | 3.4 | 13% | 38% | 0% | 2.0 |
| End period | A | Average value period | 2.0 | 2.5 | 4.8 | 7.3 | 7.4 | 0% | 0% | 0% | 2.5 |
| | | Change End vs Start period | −1.8 | 0.1 | −0.8 | 1.4 | 4.0 | −13 p.p. | −38 p.p. | 0 p.p. | 0.5 |

The result shows a significant improvement in the clinical effect of the combination product, A+B compared to A. The level of clinical effect, concerning the measured symptoms was substantially improved for patient 1 in comparison to patient 3.

The result also shows an improvement in patient safety concerning patient 2, when the decision was taken to interrupt the treatment of the PP based on the feedback information from the combination product.

Aspects Concerning Study Set-Up 1

The results clearly show the clinical effect of the combination product versus only the PP. Patient 1 using A+B, improved in all five symptoms while patient 3, using only A, improved in just two symptoms when comparing the change in perceived symptoms from the start period to the end period. A comparison of the change, direction and magnitude, for each symptom between patient 1 and 3 shows a significant better result for patient 1 compared with patient 3, where patient 1 had better improvement in four of the five symptoms. Patient 1 also improved the perceived level of Quality of Life, meanwhile Patient 3 just improved slightly. Some aspects of the result:

- The set of functions in the QFM was crucial in order to take adequate health care decisions based upon the answers from the patients to the set of questions.
- Feedback, which was a central part of the QFM, to the patient was necessary in order to gain clinical effect. When the patient got feedback on his/her answers to the set of questions, the patient's dosage of the PP was changed, which led to an increased clinical effect. The amount of side effects decreased as well.
- The possibility to improve the efficacy in individualizing the dosing administration of the used PP increased substantially using the combination product, A+B. To achieve that, a QFM developed for the specific PP and the conditions of the patient, was crucial.

Review of Patient Outcomes in Set-Up 1

A central aspect with the actual PP is the titration in order to find the optimal dose for a specific patient and in this study there are several different dosing levels. In ordinary health care titration is very seldom realized. The invention, i.e., the combination product enables a new and efficient way of individualizing the dose for the specific conditions of the patient, which was seen in this study. This will be clear in the following detailed review.

Patient 1: A detailed evaluation of patient 1 for the treatment period better shows how the invention works.

During the first phase patient 1 showed symptoms of GAD and relatively low levels of side effects, with exception of dry mouth. On the basis of the answers from patient 1, feedback information generated from the set of functions indicated that a change in dosage for the actual patient would have been positive. This feedback was communicated back to patient 1.

During the second phase, now with a higher dosage of the PP, there was no improvement in two of the symptoms, but a sharp decline in the others. The side effects remained on a stable level, with a decrease in dizziness. On the basis of this information, the set of functions indicated another increase in dosage of the PP, this feedback was then communicated to patient 1.

During the third and last phase, with an even higher dosage of the PP, there was a significant improvement in two of the symptoms while the three others remained stable. The side effects decreased substantially.

The outcome of the treatment with the combination product, A+B, showed positive results comparing the start period with the end period. All five symptoms improved significantly and with no side effects with the exception of one, mouth dryness, which decreased with 50 percentage points. The perceived quality of life substantially increased compared to baseline.

Patient 3: A detailed evaluation of patient 3 for the treatment period shows a different development than for patient 1.

During the first phase patient 3 showed significant symptoms of GAD. The side effects were relatively low. There was no set of functions, no change in dosage of the PP, and no generated or communicated feedback to patient 3.

During the second phase the status of patient 3 was basically similar to the first one, but with two changes. There was deterioration in two of the symptoms and a significant decrease in the side effects. But the patient had no access to the CPP so there were no set of functions, no change in the dosage of the PP, and no feedback to patient 3.

During the third and last phase there was an improvement in two of the symptoms, but the other three remained on approximately same levels which were relatively high. The side effects were totally reset, implying a substantial decrease compared with the start period. The result of the treatment with the PP showed a mixed effect. A comparison between the start and the end period showed an improvement in two symptoms, deterioration in three symptoms, and no visible side effects at the end. The perceived Quality of Life was slightly higher in the end compared to start period.

Aspects Concerning Study Set-Up 2

The results clearly show the clinical effect of the combination product versus only the PP concerning patient safety.

Due to the fact that patient 2 is interrupted using the PP during the study period, the evaluation of patient 2 in comparison to patient 3 is of less value. This is due to the fact that the evaluation circumstances for patient 2 changes, meanwhile the circumstances for patient 3 are stable.

The evaluation of patient 2 is made on the basis that what would have been the case concerning the clinical result and patient outcome if there would have been no set of functions and no feedback to the patient. If there would have been no set of functions and no feedback to patient 2, the patient would have continued to take the PP for a period of time. Due to this, the comparison of the patient 2 development will be made between the phase after the interruption and the period before.

Some aspects of the result:
- The combination product gave an improved patient safety. There was a significant improvement in both symptoms and decrease in side effects when patient 2 interrupted taking the PP. This was especially valid for three of the symptoms and all of the side effects.
- The combination product, especially the QFM, was crucial in the change of using PP for patient 2. Based upon the answers to the set of questions, the feedback information generated by the set of functions indicated a change in the medication—an interruption of taking the PP. This feedback information was then communicated to the patient by the healthcare personnel
- Even though patient 2 interrupted taking the PP, all five symptom values were either improved or in parity with the values during the first period. The effect of using A+B, despite the interruption of taking the PP, was positive to the patient. The corresponding situation was valid for the defined side effects.
- In a comparison between patient 2 and 3, the most significant result was the dramatic change due to the interruption of taking the PP. Meanwhile patient 3 had a relatively stable development, patient 2 experienced a comprehensive change in both symptoms and side effects during the study period. A central aspect of this was the importance of the individualization enabled by the invention, and the need for a PP and patient adapted QFM permitting an individualization of the PP treatment in clinical practice.
- For the complete period patient 2 improved in three symptoms and was stable in two, meanwhile patient 3 improved in one symptom, was stable in two, and deteriorated in two.

Review of Patient 2 Outcomes in Set-Up 2

During the end of the first phase the patient showed substantially deteriorations in two symptoms, improvements in two and stability in one. The side effects remained relatively high and slightly increasing. Based upon the answers from the patient, the feedback information from the set of functions indicated that the intake of the PP should be interrupted, which then was communicated to the patient through the feedback information.

During the second, and last, phase the patient was using only "B". There was a substantial improvement in two of the symptoms and stabilization in the three others in comparison to the levels of the variables before the interruption. The levels on all measured side effects were substantially improved.

Aspects Concerning Study Set-Up 3

The results concerning non-adherence to antidepressant medication in patients with anxiety disorders, in two other published scientific studies, are reported to be 53%-70%. References: Sheehan D V, Keene M S, Eaddy M et al. *CNS Drugs.* 2008; 22, *"Differences in medication adherence and healthcare resource utilization patterns: older versus newer antidepressant agents in patients with depression and/or anxiety disorders."* and Stein M B, Cantrell C R, Sokol M C et al, *Psychiatr Serv.* 2006; 57, *"Antidepressant adherence and medical resource use among managed care patients with anxiety disorders."*

The average adherence to the PP concerning the patients in the intervention group was 93% which was significantly higher than the adherence to the medication for the patients in the above mentioned studies.

Even though the results from the different studies are not directly comparable due to different conditions, it is obvious that the invention in the anxiety disorders area should lead to a substantial improved adherence to a medication.

Aspects Concerning the Invention

From the results from both set-up 1 and 2, one conclusion is that the invention was central in order to achieve the results. The QFM had to be developed specifically to adapt both to the specific PP and to the patient's conditions and circumstances.

From set-up 1 it was clear that using the communication tool and the adapted QFM it was possible to improve the clinical effects of the specific PP. The specific clinical aspects of the PP were taken into consideration in the QFM and based upon the collected data and the generated feedback information, it was possible to take a decision to change the dosage of the PP. This decision was then communicated to the patient and the titration led to a positive clinical result.

In a similar way, the QFM had to be adapted to the conditions of the patient.

The results from set-up 2 illustrated in a similar way the positive effect of using the invention, including an adapted QFM, to both the specific PP and to the conditions of the patient. The decision to interrupt the medication of the actual PP was based upon the information collected through the QFM. The decision was then communicated to the patient and the result led to improved patient safety. Without the invention and an adapted QFM, it would not have been possible to get these results.

The invention makes the continuous follow-up of side effects and adverse events possible in clinical practice. The invention realizes an efficient way to detect and react on the emergence and development of side effects and adverse events.

Study 4: Ticagrelor and Acute Coronary Syndromes

Background

In this example the treatment is a combination product consisting of Brilinta, the prescribed Pharmaceutical Product (PP), integrated with an interactive patient communication tool, i.e. the Computer Program Product (CPP), in accordance with the invention.

A study will be performed as described below to substantiate the efficacy of the treatment and invention. The study shall comply with national and international rules, legislation and practices with regards to e.g., ethics, informed consent, protection of confidential personal information, reporting of side effects and adverse events.

Brilinta is a medicine that contains the active substance ticagrelor. It is available as round, yellow tablets (90 mg). Brilinta is used together with aspirin to prevent atherothrombotic events (problems caused by blood clots and hardening of the arteries) such as heart attacks or strokes. It is used in adults who have had a heart attack or have unstable angina (a type of chest pain caused by problems with the blood flow to the heart). The medicine can only be obtained with a prescription.

Actual study population is patients with Acute Coronary Syndromes (ACS) or suffering from a myocardial infarction.

Study Objectives

The study objectives are to improve the clinical effect of the used PP, improve patient safety, and increase the patients' perceived quality of life.

The study objectives are evaluated based on the following measurements:

- Prevent atherothrombotic events; increase the time to next myocardial infarction
  - Heart attack
  - Stroke
- Control and decrease the amount of adverse events and side effects. This includes minimizing the following side effects:
  - Dyspnoea (difficulty breathing)
  - Epistaxis (nosebleeds)
  - Gastrointestinal haemorrhage (bleeding in the stomach or gut)
  - Bleeding in the skin or below the skin
  - Bruising
  - Bleeding at the procedural site (where a blood vessel has been punctured)
- Improve the perceived Quality of Life and wellbeing.

The secondary aims concerning the studied treatment are:
- Improve adherence to the medical treatment with the PP
- Support lifestyle changes that have positive impact on the chosen medical treatment
  - Smoke cessation (for smoking patients)
  - Improved diet
  - Improved physical activity Study Design and Set Up The study project is an open randomized study. The project comprises a total of 20 patients that will be offered access to the combination product with a specific question-feedback model (QFM). A control group is randomly chosen to be followed and receive only standard treatment and standard support in clinical practice according to ordinary health care. The patients will continuously during the study period receive questions and information through their mobile phones and computers in accordance with the set of questions specified below. The CPP and the QFM will be set up and developed in accordance with the descriptions in the documentation of the already performed studies. The specific QFM in this study will of course differ from the ones used in those studies because of the specific conditions of the chosen PP, the therapy area, and the patient group, etc.

Actual PP: Brilinta, co-administered with acetylsalicylic acid (ASA).

Study length: 12 months.

Design: Open controlled study.

Population: Men and women with ACS.

Number of patients: 10 patients each in the intervention group and in the control group.

Control group: Patients taking only Brilinta, co-administered with acetylsalicylic acid (ASA).

Examinations: Evaluation according to standard practice.

Sampling: Sampling according to standard practice.

Patients with ACS or suffering from a myocardial infarction are informed about the study and the possibility to enter the study. Patients willing to participate are consecutively included. Patients in the intervention group will receive a short introduction of the communication tool. If necessary, patients will be able to contact technical support for the tool. If a patient included by medical staff does not start using the tool, the tool will automatically contact the patient to offer technical support, subject to approval of the patient.

At the beginning the patient fills out a questionnaire relating to basic facts about his/her personal situation and health situation, his/her commitment to treatment, perceived commitment from medical staff, quality of life, consent to staff to retrieve data from the patient's medical records and to participate in the study. Weight, length, waist-measure and blood pressure are measured and recorded at inclusion in the study. After 12 months the same questions are asked again and the intra-individual change is calculated. Patients are informed that they shall contact medical staff if they become acutely ill or if their condition seriously deteriorates.

Criteria for inclusion:
Undergone Myocardial Infarction or unstable angina.
Access to a mobile phone capable of handling the used CPP.

Criteria for exclusion:
Patients unable to answer the questions through a mobile phone.

Description of the Used Communication Tool and Computer Program Product

A similar communication tool and computer program product as the one used in the earlier presented and performed studies will be used. See the earlier presentation of that tool for more basic details. In some areas the communication tool used in this study will differ from the earlier used one:

- Improved and more distinct feedback, both to patients and to the healthcare personnel. The feedback will contain more valuable information, be easier to access and understand, and will be accessible in a variety of formats.
- Improved set of functions enabling a wider possibility to identify and react upon a number of different situations concerning clinically relevant information of the specific PP, impaired progress of the patient's health situation and improved situation implying positive feedback.

The Question-Feedback Model

The Set of Questions

The set of questions will be presented to the patients according to a predefined grouping of the questions and a question schedule. The set of questions will be developed and adapted to the specific PP, Brilinta.

Patient Education and Awareness

The set of questions will also take into account that patient education and health awareness are important factors for patients taking the specific PP, Brilinta, especially including areas as:

Risk factors related to lifestyle, including:
  Cigarette smoking.
  Diet and diabetes.
  Low exercise.
Recognition of symptoms.
Awareness and development of medical treatment and health situation, including adherence to Brilinta and treatment.

The invention can support patient education and increased awareness by, among other things:

Visualize the patient's health evolvement and important relationships.
Remind patients about their medication schedule and to increase adherence to Brilinta.
Help patients to understand and detect symptoms, side effects, and adverse events of Brilinta.
Support smoke cessation.
Support diet changes.
Support improved physical activity.

Individualization of the Set of Questions

The questionnaire regimen is possible to individualize according to the following aspects:

Remove some groups of questions based upon the circumstances of the specific patient
  Smoking cessation
  Extra need for improved levels of physical activity
  Extra need for improved diet
Change the response times for the questions, i.e., when the patient will be reminded to answer the questions and the current questions will appear on the patient's mobile phone.

Within each group the questions themselves are possible to further individualize.

Starting Set of Questions and Question Schedule

The questions will be given to the patients following the questions schedule as seen in table 23. This is the starting set of questions. Depending on each patient's development over time of the Brilinta treatment, it can be updated in order to incorporate the specific clinical outcome. Both an update of the general set of questions and a particular update of the specific set of questions for each patient will most probably be performed, depending on clinically relevant information for the PP.

Some questions might also have different kind of dependencies, e.g., depending on the answers the questions and question schedule might alter.

TABLE 23

Questions and question schedule (illustrative)

| Question group | Compulsory | Question schedule | Examples of questions |
|---|---|---|---|
| General health status | Yes for all patients | Month 1-2: Every second day Month 3-4: Every fourth day Month 5-6: Once a week | 1. "How do you feel?" (VAS 0-10; 0 = Extremely bad, 10 = Extremely good) 2. "Are you experiencing stress right now?" (VAS; 0 = Not at all, 10 = Extremely much) 3. "Did you feel well rested this morning?" (VAS; 0 = Not at all rested, 10 = Extremely well rested) 4. "Physical exercise today, example?" (Multiple choice; Sat still/Standing/Partly walking/Walking a lot/Hard physical working) 5. "What is your current daily dose of Brilinta? [mg]" (Numeric) 6. "Do you take Brilinta according to the agreed prescription?" (Multiple choice; Yes/Yes, partially/No) 7. "Have you had any social activities today?" (Multiple choice; Yes/Yes, partially/No) 8. "Do you smoke? (Multiple choice; Yes/Sometimes/No" [This question will be given only twice] |
| Smoke cessation | For patients answering Yes or Sometimes on question #8 in the group General health status. | Month 1-2: Every second day Month 3-4: Every fourth day Month 5-6: Once a week | 1. "How many cigarettes have you smoked today?" (Numeric) 2. "Your cravings for smoking today?" (VAS; 0 = None, 10 = Worst possible) 3. "How motivated are you to be smoke free?" (VAS; 0 = Not motivated at all, 10 = Highly motivated) 4. "Do you have medicine for smoke cessation? (Multiple choice; Yes/No) 5. "Do you take the medicine for smoke cessation according to the agreed prescription?" (Multiple choice; Yes/Yes partially/No) 6. "Are you satisfied with your effort to quit smoking?" (VAS 0-10; 0 = Can be a lot better, 10 = Done my best) 7. "Symptoms of urge to smoke?" (Multiple choice; Irritable/Depressed/Restless/SleepDisorders/Anxiety/Hunger/Concentration problems) 8. "Out of breath last week?" (VAS 0-10; 0 = Not at all, 10 = Very much) 9. "Cough from smoking the last week?" (VAS 0-10; 0 = No, 10 = Very much) |
| Blood pressure and Bleeding | Yes for all patients | Week 1-2: Every second day Week 3-24: Once a week | 1. "Your systolic blood pressure today?" (Numeric) 2. "Your diastolic blood pressure today?" (Numeric) 3. "Have you felt something of the following?" (Multiple choice; Dyspnoea (difficulty breathing)/Epistaxis (nosebleeds)/Gastrointestinal haemorrhage (bleeding in the stomach or gut)/Bleeding in the skin or below the skin/Bruising/Bleeding at the procedural site (where a blood vessel has been punctured)) |
| General health, treatment | Yes for all patients | Month 1-3: Once a week Month 4-6: Bi-weekly | 1. "How have you slept this week?" (VAS 0-10; 0 = Extremely poor, 10 = Extremely good) 2. "How much have you been exercising this week, compared to your maximum capability?" (VAS 0-10; 0 = Nothing at all, 10 = At my maximal capacity) |

TABLE 23-continued

Questions and question schedule (illustrative)

| Question group | Compulsory | Question schedule | Examples of questions |
|---|---|---|---|
| | | | 3. "To what extent has your health situation affected your activities this week?" (VAS 0-10; 0 = Not at all, 10 = To a very large extent)<br>4. "Your weight this morning?" (Numeric)<br>5. "Your quality of life as regards to health?" (VAS 0-10; 0 = Extremely bad, 10 = Extremely good)<br>6. "To what extent has your health situation affected your activities this week?" (VAS 0-10; 0 = Not at all, 10 = To a very large extent)<br>7. "Your weight this morning?" (Numeric) |
| Side effects and adverse events | Yes for all patients | Month 1-3: Once a week<br>Month 4-6: Bi-weekly | 1. "Is your pulse extremely low (less than 60 beats/second)?" (Multiple choice; Yes/Maybe/No)<br>2. "Do you feel short of breath?" (VAS 0-10, 0 = Not at all, 10 = Very much)<br>3. "Have you had any bleedings in the following places recently?" (Multiple choice; Nose/Urine/Feces/Eyes/Cough/Vagina and not menstrual/Strong at wounds/Other strong bleeding/None)<br>4. "Have you had any of the following symptoms recently? (Heart attack)" (Multiple choice; Chest/Discomfort in the Upper Body/Cold Sweats/Shortness of breath/Radiating pain down the left arm/Squeezing chest pains/Queasiness/Nausea/Upper abdominal pain/Weakness/Unusual fatigue/Lower chest pain/Indigestion like symptoms/Upper back pain)<br>5. "Have you had any of the following symptoms recently? (Stroke)" (Multiple choice; Sudden numbness or muscles contraction of the arm or leg, especially on the left side/Sudden fumbling in normal speaking or a feeling of tied tongue/Sudden drop in vision with gloomy screen/Sudden feeling of severe headache with no reason/Loss of balance in normal walking/Loss of sufficient strength to stand fast/Loss of consciousness with fatigue/Breathing trouble/Seizures like fits or spasm)<br>6. "Have you had any of the following side effects recently?" (Multiple choice; Headache/Dizziness/Abdominal pain/Diarrhea/Nausea/Rash/Itching/Gastritis)<br>7. "Have you had any of the following side effects recently?" (Multiple choice; Constipation/A tingling feeling/Confusion) |
| General food and diet | Yes for all patients | Week 1-24: Every second week | 1. "Number of standard measures of alcohol last 24 hours?" (Numeric)<br>2. "Portion size of breakfast today?" (VAS 0-10; 0 = Very small, 10 = Very large)<br>3. "Cooked meal for lunch today?" (Multiple choice; Yes/No)<br>4. "Portion size of lunch today?" (VAS 0-10; 0 = Very small, 10 = Very large)<br>5. "Portion size of dinner today?" (VAS 0-10; 0 = Very small, 10 = Very large)<br>6. "Are you satisfied with your diet?" (VAS 0-10; 0 = Not at all satisfied, 10 = Extremely satisfied)<br>7. "Are you satisfied with your treatment?" (VAS 0-10; 0 = Not at all satisfied, 10 = Extremely satisfied) |
| Physical activity | For patients who need extra support to improve their physical activity level | Month 1: Every second day<br>Month 2: Twice a week<br>Month 3-6: Once a week | 1. "How physically active have you been today?" (VAS 0-10; 0 = Nothing at all, 10 = At my maximal capacity)<br>2. "To what extent, in number of minutes, have you been physically active today?" (Numeric)<br>3. "What activities have you performed today?" (Multiple choice; Lying/Sitting/Standing/Walking/Walking a lot/Almost running/Running/Hard physical working)<br>4. "Do you feel more interested in performing physical activities today than a couple of days ago?" (Multiple choice; Yes definitely/Yes, a bit/Either or/No, not really/Not at all)<br>5. "Are you satisfied with the forms of exercise you perform?" (VAS 0-10; 0 = Not at all satisfied, 10 = Extremely satisfied) |
| Diet | For patients who need extra support to improve their diet and food intake | Month 1: Every second day<br>Month 2: Twice a week<br>Month 3-6: Once a week | 1. "Portion size of breakfast today?" (VAS 0-10; 0 = Very small, 10 = Very large)<br>2. "Cooked meal for lunch today?" (Multiple choice; Yes/No)<br>3. "Portion size of lunch today?" (VAS 0-10; 0 = Very small, 10 = Very large)<br>4. "Portion size of dinner today?" (VAS 0-10; 0 = Very small, 10 = Very large)<br>5. "Number of standard measures of alcohol last 24 hours?" (Numeric)<br>6. "Are you satisfied with your diet?" (VAS 0-10; 0 = Not at all satisfied, 10 = Extremely satisfied) |

TABLE 23-continued

Questions and question schedule (illustrative)

| Question group | Compulsory | Question schedule | Examples of questions |
|---|---|---|---|
| Follow up (monthly) | Yes for all patients | Month 1-6: Once a month | 1. "Are you going to perform any surgery in the near future?" (Multiple choice; Yes/No)<br>2. "Have you, during the last month, been taking any of the following medications as well?" (Multiple choice; Simvastatin or Lovastatin/Rifampicin/Fenytoin, Karbamazepin or Fenobarbital/Dexametason/Digoxin/Cyklosporin/Kinidn or Diltiazem/Verapamil or a beta-blocker)<br>3. "Have you, during the last month, been taking any of the following medications as well?" (Multiple choice; Warfarin/NSAID, e.g. Ibuprofen or Naproxen/SSRI. e.g. Paroxetin, Sertralin or Citalopram/Ketokonazol/Klaritromycin/Nefazodon/Ritonavir or Atazanavir/Cisaprid/Ergotalkaloider) |
| Spontaneous | Yes for all patients | Always accessible for the patients to answer | 1. "How do you feel?" (VAS 0-10; 0 = Extremely bad, 10 = Extremely good)<br>2. "Have you had any bigger bleeding recently?" (Multiple choice; Yes/Maybe/No)<br>3. "Have you had any of the following symptoms recently? (Heart attack)" (Multiple choice; Discomfort in the Chest/Discomfort in the upper body/Cold sweats/Shortness of breath/Radiating pain down the left arm/Squeezing chest pains/Queasiness/Nausea/Upper abdominal pain/Weakness/Unusual fatigue/Lower chest pain/Indigestion like symptoms/Upper back pain)<br>4. "Have you had any of the following symptoms recently? (Stroke)" (Multiple choice; Sudden numbness or muscles contraction of the arm or leg, especially on the left side/Sudden fumbling in normal speaking or a feeling of tied tongue/Sudden drop in vision with gloomy screen/Sudden feeling of severe headache with no reason/Loss of balance in normal walking/Loss of sufficient strength to stand fast/Loss of consciousness with fatigue/Breathing trouble/Seizures like fits or spasm)<br>5. "Do you feel short of breath?" (VAS 0-10, 0 = Not at all, 10 = Very much) |

The Set of Functions

The set of functions will take into account some of the following aspects:

Calculations in order to visualize graphs and make them clear to the actual user.

The patients will be able to get patient specific and understandable feedback

The authorized and responsible healthcare personnel will be able to get patient specific information in order to make decisions regarding how to increase the clinical effect and how to improve the patient safety of the specific PP.

The patients will be given patient specific information and suggestions on how to improve the clinical effect and how to improve patient safety.

Calculations in order to find and then visualize the most interesting correlations between different outcome variables. Calculations concerning the correlation between Brilinta specific factors and variables concerning clinical effect and patient safety will be focused on.

Calculations for detecting and giving immediate response to the patient, responsible healthcare personnel, and perhaps also certain authorities, when an adverse event has occurred.

Calculations for detecting and giving immediate response to the patient and responsible healthcare personnel when a serious side effect has occurred.

Calculations for detecting and giving response to the patient and responsible healthcare personnel when the patient's health situation is evolving in a negative direction.

Calculations for detecting and giving quick response to the patient and responsible healthcare personnel when other important issues have occurred.

The Type of Feedback

The type of feedback to the patients will consist of some of the following components:

Different kind of graphs based upon the answers from the patient. The feedback to the patients will, in a structured manner, visualize the correlations between different questions/variables, e.g., the result on health status when the patient is adherent to the prescribed regimen of the PP. In the graphs, the answers from the patients will, for instance, be visualized over time. This can include grouping of several variables in common graphs. The feedback information will be accessible via the patient's mobile phone and computer.

Graphs given to or accessible for the healthcare personnel. These graphs can illustrate the correlations between central outcome variables.

The graphs can contain trend lines. These will appear when the patient has been answering questions for a certain time, e.g., some trend lines will appear after a month when enough data has been reported.

The patient's evolvement over time will be illustrated in graphs, in relation to realistic health targets for that specific patient or patient group. The health targets, developed for specific questions/variables, are based upon data from earlier clinical studies/trials performed on Brilinta. The targets will be individualized for each patient, depending on the amount of available information.

The patients will be sent short text messages based upon their health evolvement and adherence to the medication. These messages will be sent as encouraging and motivating information when the patient, e.g.:

Has fulfilled something positive, such as been adherent to the PP and/or improved their hypertension, diabetes, or blood lipids Needs a "small push" in order to improve their behavior, for example to become more adherent to the PP.

In relation to each patient's evolvement and the answers, future predictions concerning his/her health status will be developed. The future predictions will visualize possible scenarios for the patient based upon how the patient will evolve in some critical issues, for example the compliance/adherence to the PP in relation to health status and level of wellbeing.

Comparisons between the evolvement of the specific patient and other patients from clinical use of the PP will be made and illustrated for the specific patients. Based on this information the patients could see the possible development of their own health status by relating to the situation and progress of other patients.

The set of functions concerning possible adverse events and side effects for the PP will be implemented. The possible adverse events and/or side effects will be visualized for the patient depending on the safety concern. Possible adverse events will be sent by messages and possible side effects will be visualized in context with the given answers, for example in different graphs or other illustrations. The possible adverse events will be sent to responsible healthcare personnel as well.

Study 5: Ticagrelor and Acute Coronary Syndrome

A study as generally outlined in Study 4 was performed. The intention with this example is to describe the invention concerning a particularly developed QFM, Question Feedback Model, for a specific drug, which kind of technical effect in the form of clinical efficacy, that will be achieved using the invention and how the efficacy will be achieved.

QFM Overview

Users

The primary users of the described QFM are the patients. However, also Healthcare professionals are necessary since they prescribe the software part of the innovations together with the actual drug to the patient. In the example, the invention is designed to achieve clinical effect by interaction with the patient. The major part of the QFM is developed for patient interaction; all communication through the mobile phone is with the patient. The HCP uses an administrative interface on their desktop enabling a possibility to include a patient into the invention and the specific QFM. The software solution is developed based on mobile and Internet communication.

QFM Structure

The actual QFM was developed for the specific drug in order to integrate with and adapt to the drug and enhance the clinical effect of the drug and value for the particular patient group. The QFM was developed with the specific clinical and pharmacological conditions of the particular drug. The QFM consisted of the following parts, where all of them were adapted to the specific drug;

Questions given to the patients
    Feedback given to the patients, realized by the
    Set of functions for the drug Other aspects included into the QFM are the actual language adjusted for patient understanding, country specific regulatory concerns for the drug and different time zones. These will not be further described in this example.

For the specific drug, the QFM is adapted concerning the following different parameters in order to gain improved clinical effect:

The specific used questions and clinical variables.
    The used feedback messages
    The configuration of the set of functions, including:
        The used threshold types and values for respective variable.
        The motivational feedback given to the patients
        Conditions controlling the visualization of the graphical feedback, including objectives to be reached
        Schedule controlling which feedback message that will be shown given a certain condition
    Introduction flow introducing the invention to the patient given their health conditions Questions In the used QFM there were two types of questions;
    Main variables; where all patient answers on the questions were used for all type of feedback given to the patients. The primary diagnose risk factors for the patients using the specific drug.
    Secondary variables; where a subgroup of the patient answers were used for a part of the possible feedback given to the patients.

In the example the questions, and the complete QFM, were selected and designed in order to improve the efficacy of ticagrelor. Hence the questions were focused on adherence to the drug and improved level of risk variables for the specific patient category, which in this case was to prevent from cardiovascular death and improve the defined life style behavior in order to avoid further heart attacks.

The prescribed dosage regimen for ticagrelor was that it was to be taken twice a day, one tablet in the morning and one in the evening. Hence, there were two answering alternatives for the adherence questions.

The following questions were used using the described question format:

Main variables:
1. Adherence to the specific drug; multiple choice;
    If the patient took the tablet in the morning the same day
    If the patient took the tablet in the evening the same day
    The patient could answer concerning the day before as well, but not earlier than that
2. Level of physical activity; three different formats;
    Which date the patient was exercising; date
    How many minutes the patient were exercising; numerical and NRS
    The intensity level; multiple choice, medium or high
3. Weight; two different formats;
    Which date the patient measured the weight; date
    The actual weight; numerical
4. Smoking; multiple choice
    If the patient smoke
    If the patient smoke occasionally
    If the patient doesn't smoke at all Secondary variables:
5. Cholesterol/Lipids; LDL
    Which date the patient measured the cholesterol level; date
    The actual level; numerical
6. Blood glucose and HbA1c; two different variables with two question formats respectively;
    Blood glucose
        Which date the patient measured the blood glucose; date
        The actual blood glucose level; numerical
    HbA1c
        Which date the HbA1c was measured; date
        The actual HbA1c level; numerical
7. Blood pressure; two different variables with three question formats respectively;

Systolic blood pressure
- Which date the patient measured the blood pressure; date
- The actual blood pressure level; numerical Diastolic blood pressure
- Which date the patient measured the blood pressure; date
- The actual blood pressure level; numerical
- If the blood pressure were measured at home or at clinic It wasn't compulsory for the patients to answer any of the questions relating to secondary variables, implying that a non-response was an alternative as well. If the patient didn't answer the adherence question, he/she got a text message the day after indicating that the patient had forgotten to answer the question.

For the main variables the patients were given feedback both through graphs, color indications and personal messages, except for smoking. For the secondary variables Blood glucose were just given feedback through graphs, meanwhile Blood pressure and Lipids the patient were given feedback through both general messages and graphs, since they were regarded as important for the specific patient category. See further below for a more exhaustive description of the used variables.

Feedback

Feedback was given to the patients in five different ways in the used QFM:
1. Different color signals
2. Graph with the patients' information adjusted to the specific conditions
3. Personal messages given the conditions
4. Report with several values illustrated including gained results
5. Information related to treatment time All of the feedback is generated and controlled using the logic in the set of functions.

The Set of Functions

There were several aspects in the set of functions enabling the specific feedback which in turn created the clinical effect of the invention. One of these aspects were the set of functions integrated with and using threshold values in relation to the answers from the patients, for respective variable, which were defined for each variable and affected all different ways of feedback. There were several threshold values for the variables and the format included both question values, number of values and date.

The threshold values were controlling the color signals in the form of traffic light symbols for every main variable, when to show the respective color indication for the patient.

For every variable a graph was shown to the patient illustrating their own answers. In the graph the values were shown in relation to the different threshold values for the actual variable. If it was a main variable, a color indication was shown as well.

Personal messages, which were depending on the answers that the patient gave on the actual question, were given to the patient according to a specifically defined schedule. The messages were given according to the defined dates, the defined thresholds and the actual answers given by the particular patient.

In relation to every variable the patient was given information, as well, concerning how to improve their personal health. General messages, related to the time using the invention, were given to the patients in order to motivate them to improve the defined efficacy.

A personal report was given to the patient showing a graphical summary of all the specific variables and the achieved results for the patient within those. In the report the variables were illustrated by different graphs and, more importantly to gain effect, different colored symbols indicating to the patient whether they have achieved their objectives or not during the actual period using the invention. If the patient achieved the objectives for a specific variable, a green symbol was shown in the report for the variable, and if not, a red symbol was shown. The most frequently used symbol was an arrow either pointing upwards or downwards. For instance if the patient has decreased in weight, a green arrow pointing downwards was shown.

The main variables was shown in the top of the report. In order to gain effect and motivate the patient to lose weight etc., the weight graph was shown close to the graph illustrating the level of physical activity.

Description of the Variables

Adherence to the Specific Drug

Key variable concerning the purpose of the actual example. The patient answered whether he/she had taken the drug in the morning and in the evening, or not, concerning both the actual day and the day before. The days earlier than that was not able to answer in order to keep the data accurate.

The patients did get a lot of specific feedback based on their answers and the set of functions. The patients was, for instance, continuously shown the following color indication, which was dependent on a set of functions algorithm adapted for the specific drug:

The patient was shown a green indication if the patient had
- Missed at the most two tablets out of fourteen the last week; and
- Not missed to take two tablets in a row The patient was shown a yellow indication if the patient had
- Missed at the most six tablets, and at least three tablets out of fourteen the last week; or
- Missed to take two tablets in a row The patient was shown a red indication if the patient had
- Missed seven or more tablets out of fourteen the last week; or
- Missed five or more tablets in a row The patient was shown a grey indication if the patient had not started to answer the question.

A graph was shown to the patient illustrating the drug usage during the last week. The reason for showing only the last week was due to the last period of usage being the most important one concerning their health. The color indication was shown both on the start screen of the application and above the graph for the question.

The patient was given personal messages for the actual question once a week. The first week they did not get any personal messages and the second week they got two. Depending on the status of the color indication, and hence the actual threshold, the patient were given different messages.

An example of a personal message for the actual question given when the patient had a green color status was: "By taking Brilique as you do, help yourself reducing the risk of getting another heart attack—well done!" An example of a personal message with yellow color status was: "Brilique reduces the risk that you will get another heart attack. For best effect, you must take the tablet as prescribed, i.e. twice daily." and when having a red color status: "Brilique reduces the risk that you will get another heart attack, and by taking Brilique twice a day, you optimize the effect. Contact your cardiologist reception immediately if you single-handedly completed treatment". An example of a general message given in the beginning of the treatment was: "Brilique should be take morning and evening, and it need not be taken with meals. A tip to remember your pills may be to take them in conjunction with brushing. Do not forget to register in the app (e-journal) which tablets you have taken."

General health messages was given every second week except for the first period when they had a higher frequency. The very first week the patient was given four general health messages.

In the personal report the adherence to the drug was shown first with clear illustrations which particular adherence the patient did achieve in percentage for the whole period.

In the study, for a further description see below, the patients in the control group was able to use this only question as a kind of e-diary, but they didn't get the feedback in the form of the color indications, the graph, the personal messages or the report. However, they got the message if they forgot to answer the question.

Level of Physical Activity

The patient could, whenever they wanted, answer to the question on actual level of physical activity. They could select the actual date for the exercise, how long the exercise had been in minutes using a numerical rate scale and how intensive the exercise was with two alternatives; medium or high.

There were three levels of color indications;

The patient did get a green color indication if they had passed the clear threshold for the specific patient category, at least 150 minutes of medium exercise per week.

If they did not exceed that clear threshold, i.e. they did exercise less than 150 minutes with medium intensity last week, they did get a red color indication.

The patient was shown a grey indication if the patient had not started to answer the question One minute of exercise with high intensity was regarded as similar to two minutes of exercise with medium intensity. The graph illustrated through staples how many minutes the patient had exercised the last week and if they exceeded the objective of 150 minutes per week.

The patient was given personal messages once a week. The first week they did not get any personal messages. General messages were also given once a week except for the first period when they had a higher frequency.

An example of a personal message given when the patient had a green color status was: "Good job! By being as physically active as you are right now during a longer period of time, you reduce the risk of suffering from heart disease again." An example of a personal message with red color status was: "Here are a few good reasons to start walking:

Reduced risk of relapse of cardiovascular disease
Stronger bones
Improved immune function".

In the personal report, level of exercise was shown with clear illustrations which results the patient had achieved during the actual period using the invention.

Weight

The patient could, whenever they wanted, answer to the question regarding their actual weight. They could select the actual date for the measurement and register the value. During the introduction of the application the patient gave their length. Hence the application could calculate the BMI of the patient.

There were four different thresholds regarding the patient BMI; two for male patients and two for female, according to the following structure:

Male patients did get a green color indication if they were below BMI 27 at their latest weight registration and for female if they were below BMI 25.

Male patients did get a yellow color indication if their BMI was 27 or above and below 32, and for female if they were equal to, or above 25 and below 30

Male patients did get a red color indication if their weight was equal to 32 or above, and for female patients if their weight was equal to 30 or above The patient was shown a grey indication if the patient had not started to answer the question The graph illustrated through a line chart their progression concerning their weight.

The patients were given personal messages every third week. The first week they did not get any personal messages. General messages were given two every third week except for the first period when they had a higher frequency in order to increase motivation.

An example of a personal message given when a patient had a green color status was: "Good job! By losing weight, you can influence other risk factors for cardiovascular disease in a positive way: better blood glucose control, lowering blood lipids and lower blood pressure." An example of a personal message with red color status was: "Overweight is an increasingly common health problem that increases the risk of cardiovascular diseases. Lifestyle changes are the basis of treatment, and a prerequisite to be able to get a permanent weight loss and thereby decreasing the risk for a new heart attack".

In the personal report, level of exercise was shown with clear illustrations which results the patient had achieved during the actual period using the invention.

Smoking

Smoking was differently designed due to the complex way of getting the specific patients to quit smoking. The patients were asked during the introduction of the application if they were smoking or not, and they could whenever they wanted access the question and change their smoking status.

The smoking thresholds were identical to the different status of smoking;

if the patient didn't smoke a green color indication was given, if the patient smoked occasionally a yellow indication was given and if the patient smoked a red indication was given.

No graph was presented. Instead different information was given, as well as links to different smoking cessation services, in order to motivate the patient to quit smoking.

The patient was given personal messages once a week, and only if they had a yellow or red status. No personal messages were given if they were green. No general messages were given. An example of a personal message given when the patient had a red color status was: "Smoking is with dyslipidemia the single biggest risk factor for cardiovascular disease. If you stop smoking, you reduce your risk of getting a heart attack again."

Cholesterol/Lipids; LDL

The patient could, whenever they wanted, answer to the question regarding their level of LDL. They could select the actual date for the measurement and register the value. Since Lipids was regarded as a secondary question there were no threshold values defined.

The graph illustrated through a line chart their progression concerning their LDL. The patient was given general messages every second week starting the third week of treatment with the drug. An example of a general message was: "Through lifestyle changes, you can increase the effect of the medication prescribed by your doctor, and to improve your blood fat is one of the most important things to lower your risk of another heart attack".

Blood Glucose and HbA1c

The patient could, whenever they wanted, answer to the questions regarding their level of Blood glucose and HbA1c. They could select the actual date for the measurement and register the respective value. Since Blood glucose and HbA1c were regarded as secondary questions there were no threshold values defined.

There were two line charts, one for each variable, in the graph illustrating their progression concerning their blood glucose. There were no messages given to the patient.

Blood Pressure

The patient could, whenever they wanted, answer to the questions regarding their levels of Blood pressure. They could select the actual date for the measurement, register the respective values and select whether the measurements were performed at a clinic or at home. Since Blood pressure was regarded as secondary questions there were no threshold values defined.

The graph illustrated through two line charts their progression concerning the Blood pressure. The measurement in clinics were shown without line charts.

The patient was given general messages every week starting the second week of treatment with the drug. An example of a general message was: "It takes a few weeks to get the full effect of your blood pressure treatment, but you can already start with the other changes required to reach your target blood pressure. A good first step could be a daily walk".

Description of the Performed Clinical Study Evaluation

The purpose of the performed clinical study was to evaluate the invention versus the usage of just the actual drug.

The study design was two different patient groups with at least eighty patients in each group. The group using the invention, hereafter called the active group, used their own mobile phones to use the QFM described above and the actual drug Ticagrelor. The other group, hereafter called the control group, used their own mobile phones with just an e-diary (control app) and the actual drug Ticagrelor.

Study design: Randomized Controlled Trial with two different patient groups

Intervention to evaluate: The invention using the above described QFM in the patients mobile phones, integrated with the actual drug Actual used drug: Ticagrelor (Brilique)

Control: e-diary. The e-diary consisted of the following items and functionalities, enabling data for study evaluation The questions concerning adherence to the specific drug, being able to answer whether the patient took the drug in the morning and/or in the evening, for the actual day and the day before.

A reminder through a text message if the patient missed to answer the adherence questions during one day Patient group: Patients with newly reported Acute Coronary Syndrome (ACS).

Number of patients in total: 166

Length of using the invention: Six months

Primary objective: Assess the non-adherence to the drug according to the prescription recommendation in patients using the invention compared to patients who only use the control-app The primary endpoint definition was according to the following: Composite endpoint of adherence failure- or treatment gap events registered by patients Adherence failure events;

More than 14% missed doses during an observation cycle of 7 days. The first missed dose of the drug initiates an observation cycle of 1 week. If a second missed dose is registered within this week an adherence failure event is registered. The third missed dose initiates a new observation cycle, and the process restarts.

Treatment gap events;

patient reported gaps of more than 4 consecutive doses

Secondary objectives: Comparison between active group and control group concerning;

Adherence to treatment of the specific drug

Cardiovascular risk factors:
BMI
Physical activity
Blood pressure
LDL-cholesterol
Smoking cessation Quality of life (EQ5D-VAS)

The patients with ACS was randomly selected to one of the study arms. After inclusion patients in the active group used the described QFM in relation to the actual drug during the actual period of time. The design of the study was similar to an ordinary clinical practice and hence minimal and ordinary communication between the HCP and the patients was performed during the study.

Results of the Clinical Study

The results of the performed study described above were substantial. Primary endpoint result, number of events, was: Active group 16.6 vs. Control group 22.8.

Secondary endpoint results, according to respective variable and change in active versus control group:

Adherence to treatment; 96% vs. 85%.

BMI; Patients having a BMI >30 decreased in average 5% in weight

Physical activity improvements; 50% vs. 32%

LDL; −1.8 vs. −1.0

Smoking cessation; −80% vs. −45%

Quality of life; +14.7 vs. +8.4

No patients in the study died during the usage of the invention, which could be seen as an effect of the increased adherence of the drug and improved secondary prevention. In comparison studies typically 3-4% of the patients lost their lives during the actual period of time.

The invention claimed is:

1. A method for treatment or prevention of Acute Coronary Syndrome comprising use of ticagrelor in combination with a computer having installed thereon a computer program product, the method comprising:
providing, to a first patient undergoing an administration and dosing regimen with ticagrelor, a first set of questions according to a question schedule, wherein the first set of questions is specific to ticagrelor;
collecting first answers to the first set of questions from the first patient;
subjecting the first answers to a first set of functions specific for the first set of questions and ticagrelor thereby generating patient-specific feedback information;

adjusting a ticagrelor dosage based at least in part on the patient-specific feedback information; and administering the adjusted ticagrelor dosage as part of an updated administration and dosing regimen to lower Low Density Lipoprotein (LDL) levels in blood of the first patient.

2. The method according to claim 1, further comprising extracting clinically relevant information from the first answers and providing the clinically relevant information to a database adapted for collecting clinically relevant information during clinical use of ticagrelor.

3. The method according to claim 1, further comprising:
a) providing a second patient and a further respondent with sets of questions specific for ticagrelor;
b) collecting second answers to the sets of questions from the second patient and the further respondent;
c) subjecting the second answers to a second set of functions specific for the sets of questions and ticagrelor thereby generating second patient-specific feedback information;
d) providing the second patient-specific feedback information to the second patient and the further respondent;
e) extracting clinically relevant information from the second answers;
f) providing the clinically relevant information to a database adapted for collecting clinically relevant information during clinical use of ticagrelor;
g) obtaining at least one of a revised set of questions or a revised set of functions by subjecting at least one of the sets of questions or the second set of functions to a review based on clinically relevant information collected during clinical use of ticagrelor; and
h) repeating steps a)-g) for a duration of treatment.

4. The method according to claim 3, wherein the review is based on information collected from the second patient.

5. The method according to claim 3, wherein the review is based on information collected from more than one patient clinically using ticagrelor in combination with the computer program product.

6. The method according to claim 3, wherein the review is based on clinically relevant information obtained during at least one of clinical trials of ticagrelor or commercial use of ticagrelor.

7. The method according to claim 1, wherein the first set of questions are related to patient compliance to at least one of a preferred dosage, a prescribed dosage, or an administration regimen of ticagrelor.

8. The method according to claim 1, wherein at least a subset of the first set of questions are related to an indication of at least one of a possible occurrence or development of at least one of an adverse event or side effect.

9. The method according to claim 1, wherein at least a subset of the first set of questions are related to a quality of life of the first patient.

10. The method according to claim 1, wherein at least a subset of the first set of questions is related to at least one of an actual administration, an actual dosage, perceived therapeutic effects, measured therapeutic effects, test results, or a perceived quality of life.

11. The method according to claim 1, further comprising generating an updated question schedule based at least in part on subjecting the first answers to the first set of functions, wherein the first set of functions use at least one of Computer Adaptive Testing or Item Response Theory.

12. The method according to claim 1, wherein the first set of functions include at least one function selected from the group consisting of calculations of target parameters, calculations of threshold values, calculations of trend lines, prediction of development of a condition, rules for defining when to give notifications, and thresholds for defining when to give notifications.

13. The method according to claim 1, wherein the first set of questions comprises at least one question relating to an intake of ticagrelor by the first patient, and wherein the patient-specific feedback information corresponds at least in part to an adherence to a prescribed ticagrelor dosage regimen.

14. The method according to claim 1, wherein the first set of questions comprise at least one question relating to at least one of a level of physical activity, weight, smoking habits, a blood level of cholesterol, a blood level of lipids, a blood level of LDL, a blood level of glucose, a blood level of HbA1c, or blood pressure.

15. The method according to claim 1, wherein adherence to ticagrelor treatment is improved.

16. The method according to claim 1, wherein the first set of functions are related to patient compliance to at least one of a preferred dosage, a prescribed dosage, or an administration regimen of ticagrelor.

17. The method according to claim 1, wherein at least a subset of the first set of functions are related to an indication of at least one of a possible occurrence or development of at least one of an adverse event or side effect.

18. The method according to claim 1, wherein at least a subset of the first set of functions are related to a quality of life of the first patient.

* * * * *